United States Patent
Noda et al.

(10) Patent No.: US 11,123,038 B2
(45) Date of Patent: Sep. 21, 2021

(54) MEDICAL IMAGE DIAGNOSTIC APPARATUS AND MEDICAL IMAGE DIAGNOSTIC SYSTEM

(71) Applicant: Canon Medical Systems Corporation, Otawara (JP)

(72) Inventors: Koji Noda, Nasushiobara (JP); Arata Komuro, Yaita (JP); Tsuyoshi Kojima, Nasushiobara (JP); Tomoko Ishizaki, Utsunomiya (JP); Takeshi Ishii, Otawara (JP); Yuki Kato, Otawara (JP); Tomomi Nagae, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 3 days.

(21) Appl. No.: 15/980,200

(22) Filed: May 15, 2018

(65) Prior Publication Data

US 2018/0333132 A1    Nov. 22, 2018

(30) Foreign Application Priority Data

May 16, 2017  (JP) .............................. JP2017-096947

(51) Int. Cl.
*A61B 6/03* (2006.01)
*A61B 6/00* (2006.01)
*A61B 6/06* (2006.01)

(52) U.S. Cl.
CPC ............ *A61B 6/586* (2013.01); *A61B 6/4441* (2013.01); *A61B 6/4476* (2013.01);
(Continued)

(58) Field of Classification Search
CPC .. A61B 6/00; A61B 6/02; A61B 6/022; A61B 6/025; A61B 6/03; A61B 6/4035;
(Continued)

(56) References Cited

U.S. PATENT DOCUMENTS

| 6,335,905 B1 * | 1/2002 | Kabel | .............. G01S 7/527 |
| | | | 367/98 |
| 2005/0050423 A1 * | 3/2005 | Yasukawa | ............ B41J 29/38 |
| | | | 714/742 |

(Continued)

FOREIGN PATENT DOCUMENTS

| JP | 2014-10599 | 1/2014 |
| JP | 2014-61170 | 4/2014 |

(Continued)

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

According to one embodiment, a medical image diagnostic apparatus includes an imager, a mechanism, and processing circuitry. The imager is configured to image a subject. The mechanism is comprising a movable part. The processing circuitry is configured to generate an image of the subject based on an output of the imager, and perform processing for incident data based on at least one of a result of analyzing the image of the subject, or information for motion of the mechanism, wherein the incident data comprises at least one of operating sound data or shaking data of the mechanism.

20 Claims, 18 Drawing Sheets

(52) U.S. Cl.
CPC .......... *A61B 6/5205* (2013.01); *A61B 6/5264* (2013.01); *A61B 6/56* (2013.01); *A61B 6/563* (2013.01); *A61B 6/581* (2013.01); *A61B 6/06* (2013.01); *A61B 6/465* (2013.01)

(58) Field of Classification Search
CPC ..... A61B 6/405; A61B 6/4233; A61B 6/4064; G01N 23/083; G01N 23/06
See application file for complete search history.

(56) References Cited

U.S. PATENT DOCUMENTS

| | | | |
|---|---|---|---|
| 2010/0094850 A1* | 4/2010 | Oogami | A61B 6/032 |
| | | | 707/705 |
| 2011/0121969 A1* | 5/2011 | Mercer | A61B 6/581 |
| | | | 340/540 |
| 2014/0006928 A1 | 1/2014 | Hirahatake | |
| 2016/0277863 A1* | 9/2016 | Cahill | H04R 3/005 |
| 2018/0082818 A1* | 3/2018 | Meiler | H01J 35/025 |
| 2019/0277779 A1* | 9/2019 | Wuestenbecker | G01N 23/046 |

FOREIGN PATENT DOCUMENTS

| | | |
|---|---|---|
| JP | 2015-16156 | 1/2015 |
| WO | WO 2015/111512 A1 | 7/2015 |

\* cited by examiner

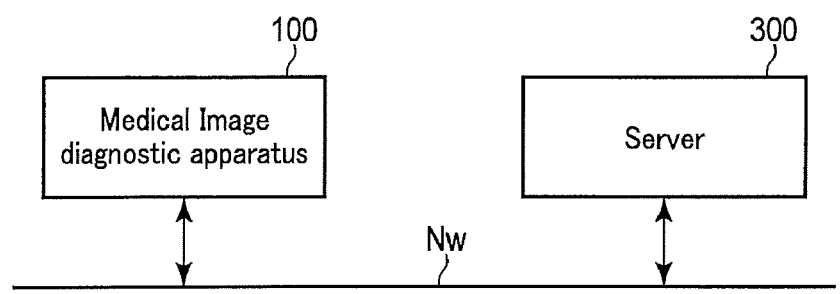
F I G. 1

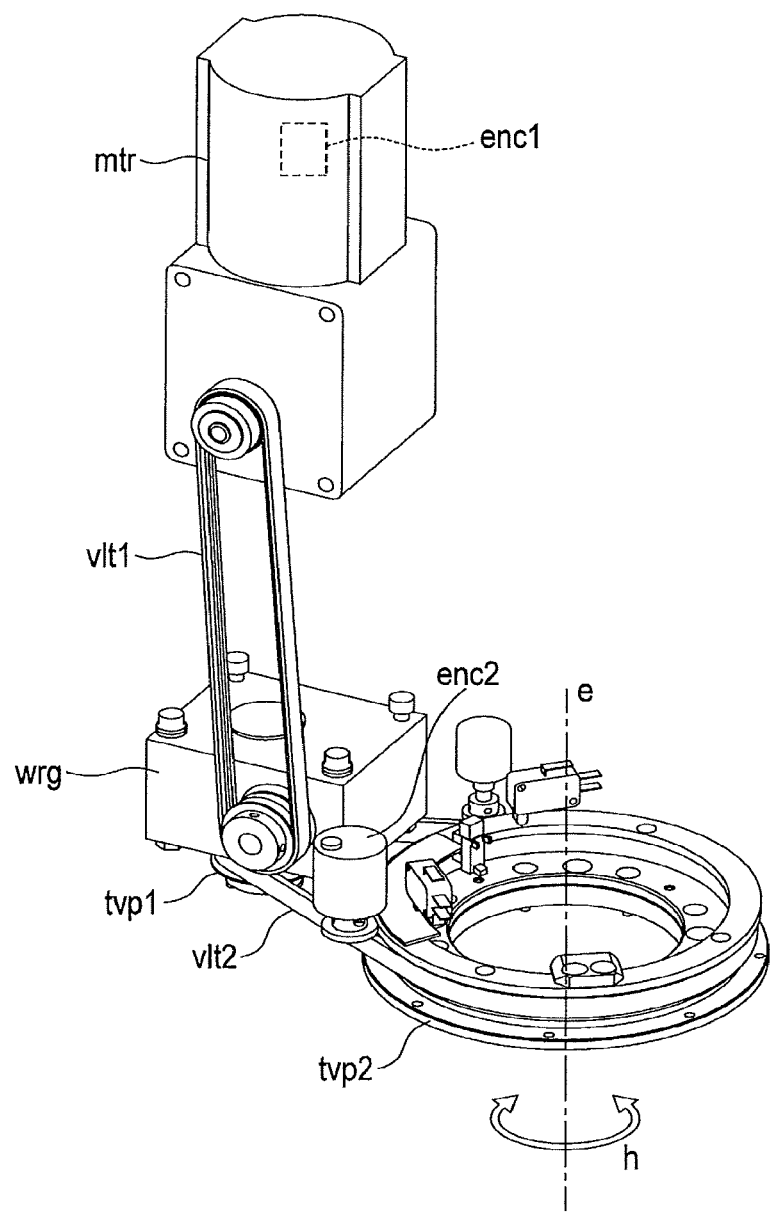
F I G. 4

FIG. 6

Table 22a

| Apparatus ID | Time | Operation | Motion axis | Position information | Rotation number | Electric-current value | Operating sound data | Error flag |
|---|---|---|---|---|---|---|---|---|
| | | | | | | | | |
| | | | | | | | | |

Table 22b

| Particular motion pattern | Motion axis | Position information | Rotation number | Operating sound data | Threshold for operating sound data | Threshold for shift amount in frequency band |
|---|---|---|---|---|---|---|
| | | | | | | |
| | | | | | | |

Table 22c

| Motion pattern | Motion axis | Start position | Goal position | Operating sound data | Motion speed | First pulse number | Second pulse number |
|---|---|---|---|---|---|---|---|
| | | | | | | | |

| Function | Threshold for pixel shift |
|---|---|
| 3D-DSA | |

| Function | Threshold for motion time |
|---|---|
| 3D-DSA | |
| 3D-LCI | |

| Acceptable value for tube focus size change |
|---|
| |

| Motion axis | Threshold for electric-current value |
|---|---|
| A | |
| B | |
| C | |

Storage 22

| Apparatus ID | Time | Operation | Error name | Error cause | Replacement component | Motion axis | Position information | Rotation number | Electric-current value | Operating sound data | Threshold | Error flag |
|---|---|---|---|---|---|---|---|---|---|---|---|---|
| | | | | | | | | | | | | |
| | | | | | | | | | | | | |

31a

| Apparatus ID | Particular motion pattern | Motion axis | Position information | Rotation number | Operating sound data | Threshold for operating sound data amount in frequency band | Threshold for shift sound data amount in frequency band |
|---|---|---|---|---|---|---|---|
| | | | | | | | |
| | | | | | | | |

31b

| Apparatus ID | Acceptable value for tube focus size change |
|---|---|
| | |

| Apparatus ID | Function | Threshold for pixel shift |
|---|---|---|
| | 3D-DSA | |

| Apparatus ID | Motion axis | Threshold for electric-current value |
|---|---|---|
| | A | |
| | B | |
| | C | |

| Apparatus ID | Function | Threshold for motion time |
|---|---|---|
| | 3D-DSA | |
| | 3D-LCI | |

Storage ~31

F I G. 8

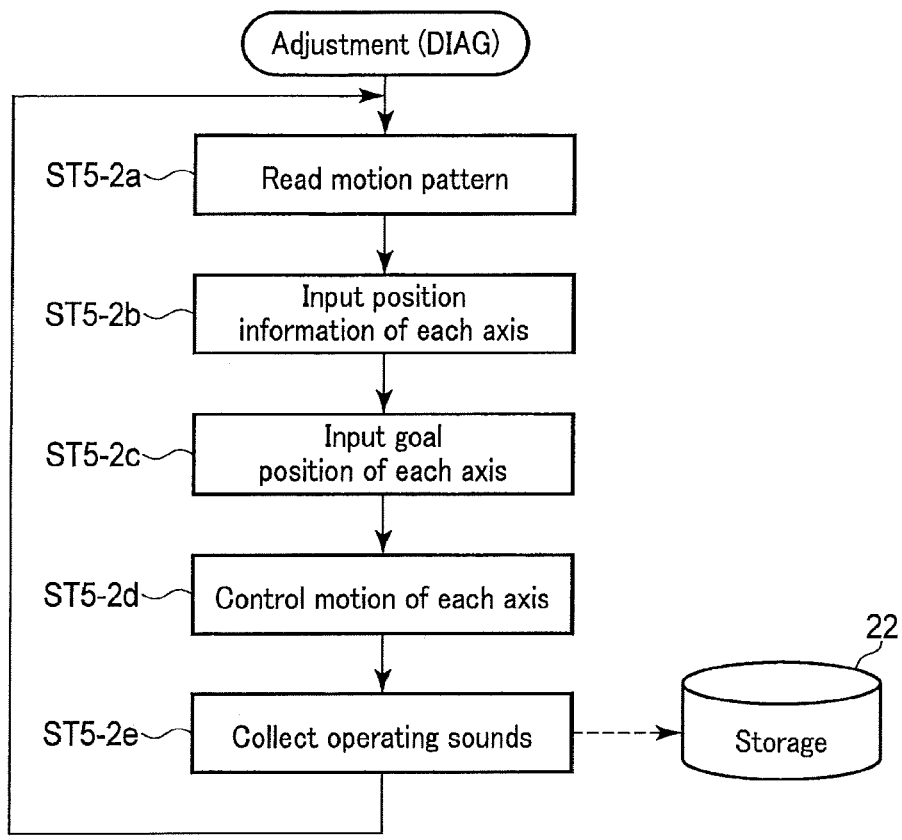
F I G. 10

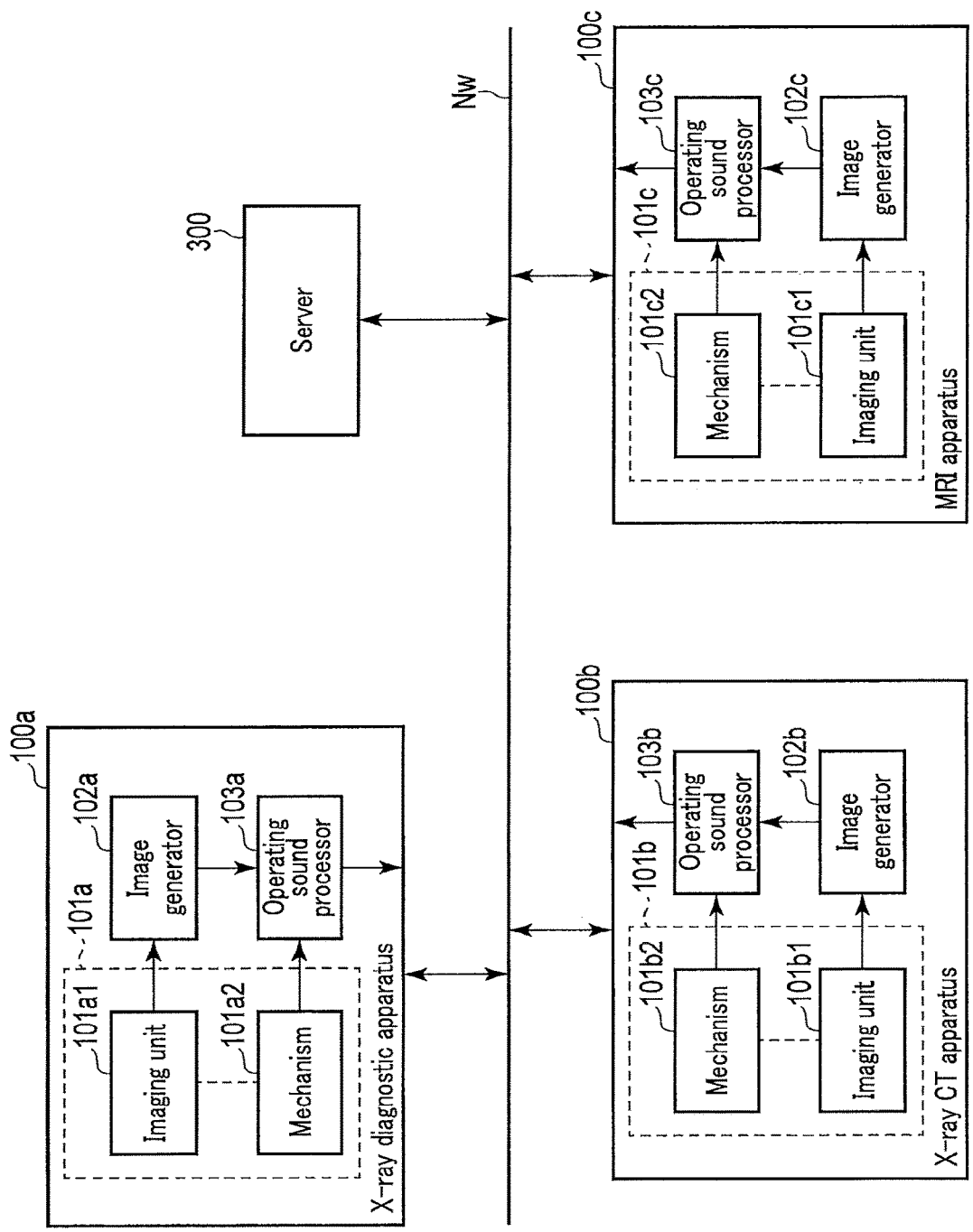
F I G. 14

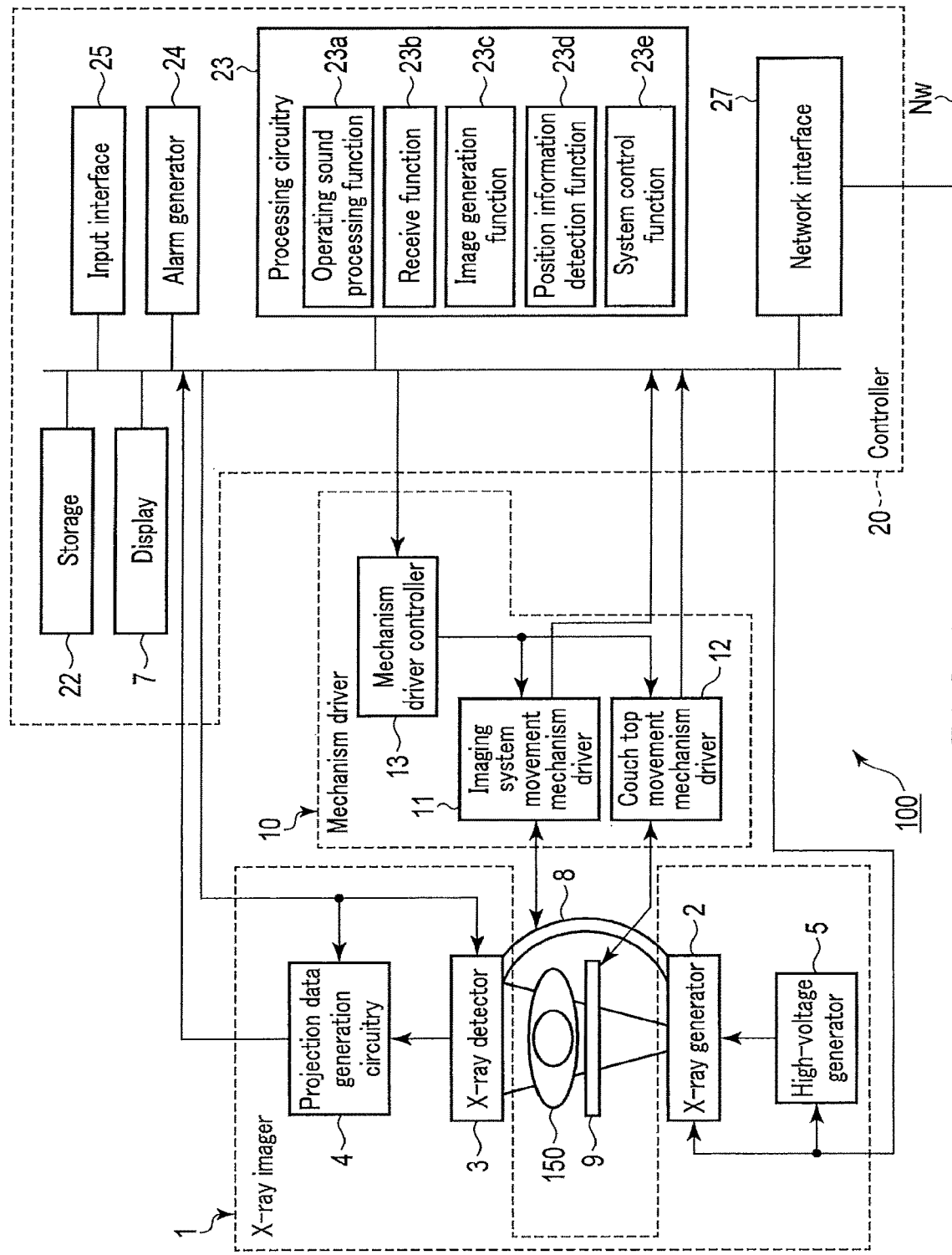
F I G. 16

MEDICAL IMAGE DIAGNOSTIC APPARATUS AND MEDICAL IMAGE DIAGNOSTIC SYSTEM

CROSS-REFERENCE TO RELATED APPLICATIONS

This application is based upon and claims the benefit of priority from prior Japanese Patent Application No. 2017-96947, filed on May 16, 2017, the entire contents of which are incorporated herein by reference.

FIELD

Embodiments described herein relate generally to a medical image diagnostic apparatus and a medical image diagnostic system.

BACKGROUND

Examples of a medical image diagnostic apparatus include an X-ray diagnostic apparatus, an X-ray computed tomography (CT) apparatus, and a magnetic resonance imaging (MRI) apparatus. While these apparatuses mutually differ in function, they share a common characteristic of generating an operating sound from a mechanical system during operations. Particulars about a medical image diagnostic apparatus that involves such a mechanical operating sound will be described, taking an X-ray diagnostic apparatus as an example.

An X-ray diagnostic apparatus generally includes a mechanical system for causing a holding portion that holds an X-ray generator and an X-ray detector to move or rotate in predetermined directions, so that X-ray imaging of a subject can be performed from a desired position or direction. The mechanical system includes a rotation mechanism for transmitting a rotating force from a drive motor to a motion axis via a power transmission mechanism. This power transmission mechanism is constituted by component pieces, such as a belt, a gear, and a chain. The "motion axis" may be called an "electric motion axis".

If such a mechanical system in an X-ray diagnostic apparatus becomes unsteady due to changes in assembly conditions, e.g., a tension or a backlash at the belt, the gear, the chain, etc., the followability of motor operations is deteriorated, and accurate positioning of an imaging system is hampered. This could result in a low image quality, as the imaging operations adopting image subtraction, etc. would produce image artifacts. Also, the degradation of image quality is not the only issue when the unsteadiness in the mechanical system is increased. An operating sound could become an abnormal noise (hereinafter, also called "abnormal sound") as well. In addition to abnormal sounds, shaking could often occur.

In the event that such an abnormal sound or the like occurs, it is necessary to perform maintenance work to quickly identify and remove the cause. In this relation, a technique to identify the cause of an abnormal sound may be, for example, the abnormal-sound detection and assessment in which characterizing components of an abnormal sound, such as a frequency and a waveform, are compared and verified with normal operating sounds. More specifically, an example technique may be to constantly transmit data of the operating sounds acquired near the X-ray diagnostic apparatus to a host side and have the host side monitor the operating sound data, so that an abnormal sound is detected and assessed based on the operating sound data.

Likewise, a technique to identify the cause of shaking may be, for example, to transmit shaking data acquired near the rotation mechanism to the host side and have it monitor the shaking data so that abnormal shaking is detected and assessed based on the shaking data. Monitoring at least either of the operating sound data or the shaking data should suffice.

However, although such an X-ray diagnostic apparatus would work without a particular trouble under normal conditions, the inventors' study has revealed that there are aspects to be improved. For example, since the X-ray diagnostic apparatus transmits at least either of the operating sound data or the shaking data at all times, the transmission quantity could be so large that the maintenance management becomes inefficient, and this can be a subject of improvement. The same applies to a medical image diagnostic apparatus other than the X-ray diagnostic apparatus, such as an X-ray CT apparatus, an MRI apparatus, or the like. Also, the same holds true not only in the instances where a medical image diagnostic apparatus constantly transmits the operating sound data and/or the shaking data to a server, but also in the instances where the medical image diagnostic apparatus constantly analyzes the operating sound data and/or the shaking data. In other words, the amount of data processed by a medical image diagnostic apparatus has been very large in both the transmission processing and analysis processing, making the maintenance management inefficient.

An object is to reduce the data amount for processing so that efficient maintenance management is realized.

BRIEF DESCRIPTION OF THE DRAWINGS

FIG. 1 is a schematic diagram showing architecture of a medical image diagnostic system according to a certain embodiment.

FIG. 4 is a schematic diagram showing an example of how a mechanical system according to the embodiment is composed.

FIG. 6 is a schematic diagram for explaining a storage of the medical image diagnostic apparatus according to the embodiment.

FIG. 8 is a schematic diagram for explaining a storage of the server according to the embodiment.

FIG. 10 is a flowchart for explaining adjustment mode operations of the medical image diagnostic apparatus according to the embodiment.

FIG. 14 is a schematic diagram showing a configuration of a first modification of the embodiment.

FIG. 16 is a schematic diagram showing a configuration of a second modification of the embodiment.

DETAILED DESCRIPTION

In general, according to one embodiment, a medical image diagnostic apparatus includes an imager, a mechanism, and processing circuitry. The imager is configured to image a subject. The mechanism is comprising a movable part. The processing circuitry is configured to generate an image of the subject based on an output of the imager, and perform processing for incident data based on at least one of a result of analyzing the image of the subject, or information for motion of the mechanism, wherein the incident data comprises at least one of operating sound data or shaking data of the mechanism.

Certain embodiments will be described using the drawings.

Figure 2:
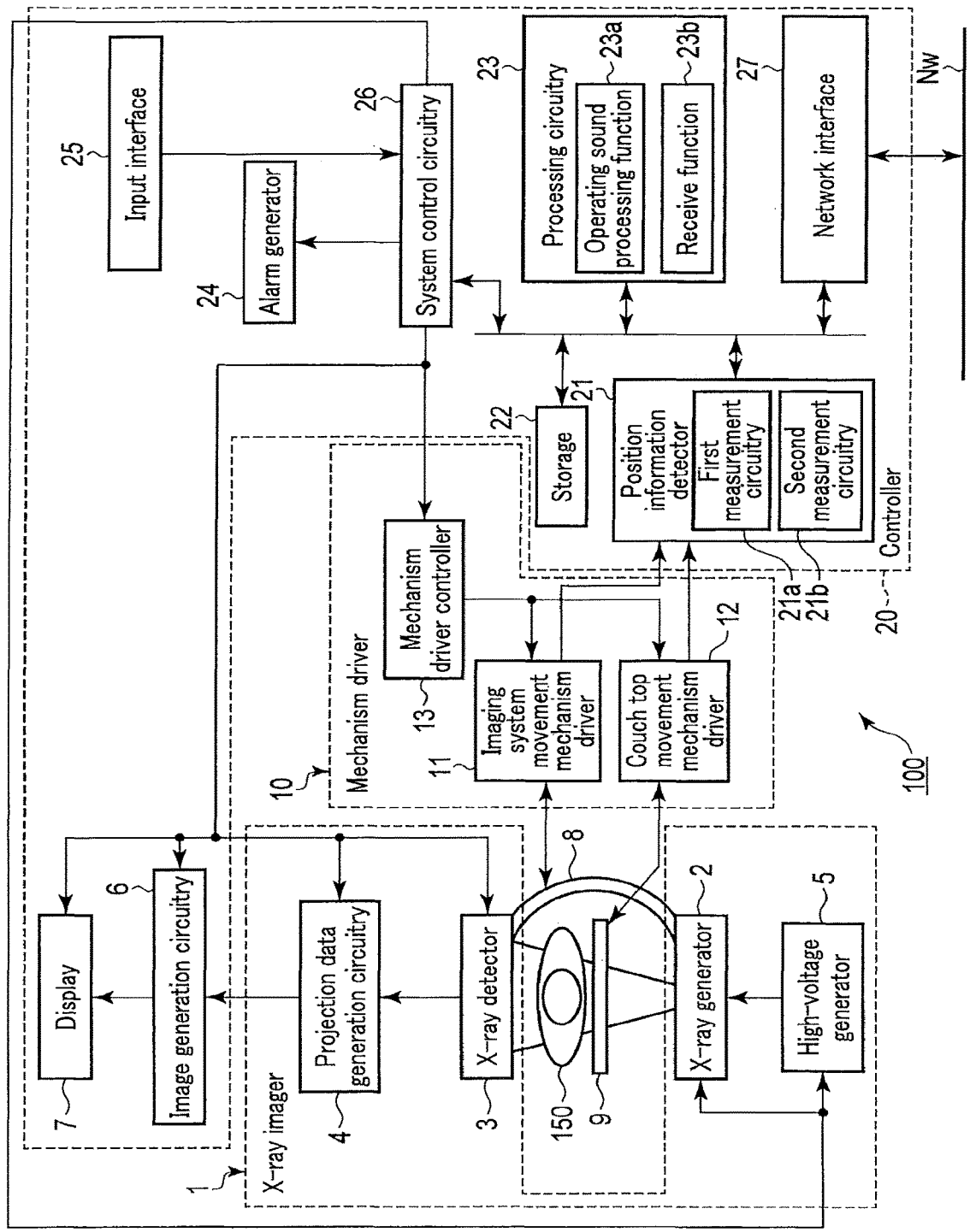
FIG. 2 is a schematic diagram showing a configuration of a medical image diagnostic apparatus according to the embodiment.
Figure 3:
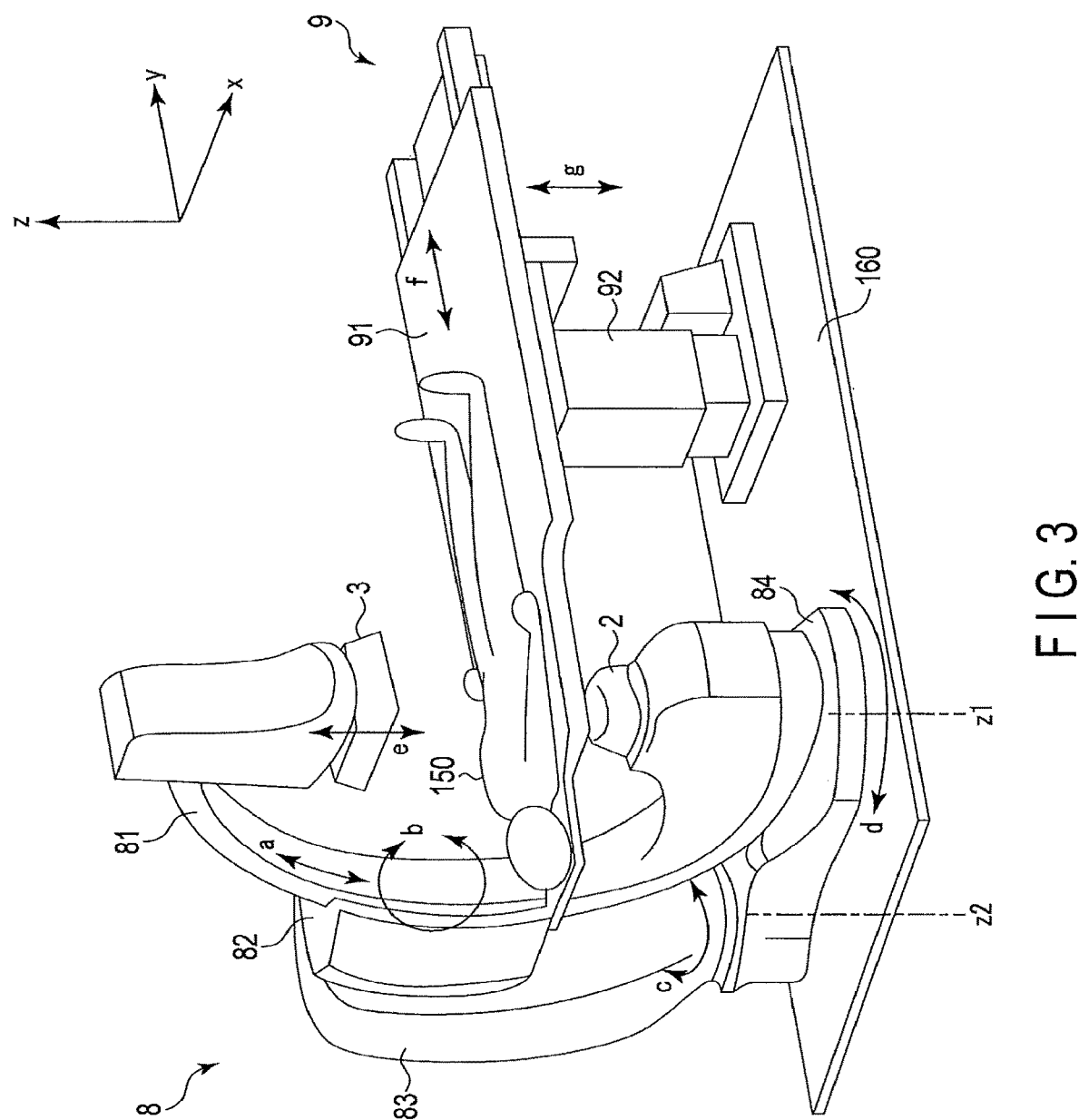
FIG. 3 is a perspective view showing structures of the medical image diagnostic apparatus according to the embodiment.

FIG. 1 is a schematic diagram showing the architecture of a medical image diagnostic system according to one embodiment. FIGS. 2 and 3 are a schematic diagram and a perspective view exemplifying how a medical image diagnostic apparatus according to one embodiment is designed. FIG. 4 is a schematic diagram showing one example of the composition of a mechanical system in the apparatus. The medical image diagnostic system includes a medical image diagnostic apparatus 100, and a server system including at least one server 300. By way of example, the following description will assume that there is one server 300. The medical image diagnostic apparatus 100 and the server 300 can communicate with each other via a network Nw. While the medical image diagnostic apparatus 100 may be any of an X-ray diagnostic apparatus, an X-ray CT apparatus, an MRI apparatus, etc., this embodiment will be described assuming that it is an X-ray diagnostic apparatus. The medical image diagnostic apparatus 100 includes an X-ray imager 1, image generation circuitry 6, a display 7, a holder 8, and a couch 9. The X-ray imager 1 (imaging unit) irradiates a subject 150 with X-rays and detects the X-rays transmitted through the subject 150 to generate projection data. The imaging subject of the imaging unit is not limited to the subject 150 but may be a phantom. The "imaging unit" may also be called an "imaging system". The image generation circuitry 6 generates image data based on the projection data. The display 7 displays the obtained image data. The holder 8 includes a holding portion for holding an X-ray generator 2 and an X-ray detector 3 of the X-ray imager 1 (imaging unit), and for moving or rotating them around the subject 150 in a predetermined direction. The couch 9 allows a couch top that carries the subject 150 thereon to move in a predetermined direction. The holder 8 includes a mechanism having a movable part for moving or rotating the holding portion. The image generation circuitry 6 constitutes an image generator to generate a subject image based on the output of the imaging unit.

Further, the medical image diagnostic apparatus 100 includes a mechanism driver 10 for supplying drive signals to later-described movement mechanisms installed at the holder 8 and the couch 9, respectively, and also includes a controller 20 for controlling the X-ray imager 1 via the mechanism driver 10. The controller 20 includes a position information detector 21, a storage 22, processing circuitry 23, an alarm generator 24, an input interface 25, system control circuitry 26, and a network interface 27. The position information detector 21 detects position information of the holding portion, the imaging system attached to the holding portion, and the couch top provided at the couch 9. The input interface 25 is for inputting subject information, setting X-ray imaging conditions including X-ray irradiation conditions, inputting various command signals, and so on. The system control circuitry 26 takes total control over these elements so that safe and efficient X-ray imaging can be performed for the subject 150. The network interface 27 may be a circuitry element for communicating with the server 300 via the network Nw.

The X-ray imager 1 includes the X-ray generator 2, the X-ray detector 3, projection data generation circuitry 4, and a high-voltage generator 5, and it has a function of generating projection data based on the amount of X-rays transmitted through the subject 150.

The X-ray generator 2 generates X-rays to irradiate the subject 150 placed on the couch top 91. The X-ray generator 2 includes an X-ray tube, and an X-ray collimator that forms an X-ray cone beam from the X-rays emitted from the X-ray tube. The X-ray tube is a vacuum tube for generating X-rays, and it applies a high voltage to electrons emitted from a cathode (filament) so that the electrons are accelerated and collide with a tungsten anode (target) to cause X-rays. The tungsten anode rotates according to the rotation of a shaft supported by a bearing. That is, the X-ray generator 2 includes a mechanism having a movable part for rotating the tungsten anode. The X-ray collimator is positioned between the X-ray tube and the subject 150, and collimates the X-ray beam from the X-ray tube into a size of a predetermined irradiation field.

The X-ray detector 3 detects X-rays transmitted through the subject 150. This X-ray detector 3 may be a type that converts X-rays directly into electric charges, or a type that first converts X-rays into light and then converts the light into electric charges. The following description will assume the former type, but the X-ray detector 3 may also be the latter type. Specifically, the X-ray detector 3 according to this embodiment includes a planar detector that converts the X-rays transmitted through the subject 150 into electric charges to accumulate, and a gate driver that generates drive pulses for reading the electric charges accumulated in the planar detector.

The planar detector includes two-dimensionally arranged micro detection elements. Each detection element includes a photoelectric film, a charge accumulation capacitor, and a thin film transistor (TFT), which are not shown in the drawings. The photoelectric film senses X-rays and generates electric charges according to the amount of incident X-rays. The charge accumulation capacitor accumulates the electric charges generated at the photoelectric film. The TFT reads the electric charges accumulated at the charge accumulation capacitor at predetermined timings. Specifically, the accumulated electric charges are sequentially read with the drive pulses supplied from the gate driver.

The projection data generation circuitry 4 includes a charge-voltage converter, an analog-digital (A/D) converter, and a parallel-serial converter. The charge-voltage converter converts the electric charges, read in units of rows or columns from the planar detector in a parallel manner, into voltages. The A/D converter converts the output of this charge-voltage converter into digital signals. The parallel-serial converter converts the digitally-converted parallel signals into time-series serial signals.

The high-voltage generator 5 includes a high-voltage generating unit and an X-ray controller. The high-voltage generating unit generates high voltages for application between the anode and the cathode in order to accelerate the thermo-electrons from the cathode of the X-ray tube. The X-ray controller controls X-ray irradiation conditions for the high-voltage generating unit, including a tube current, a tube voltage, duration of irradiation, irradiation timing, etc., in accordance with instruction signals supplied from the system control circuitry 26.

The image generation circuitry 6 includes projection data storage circuitry and image arithmetic circuitry, which are not shown. The projection data storage circuitry sequentially stores the time-series projection data supplied from the projection data generation circuitry 4 of the X-ray imager 1 so that two-dimensional projection data is generated. The image arithmetic circuitry subjects the two-dimensional projection data generated at the projection data storage circuitry to image processing, such as filtering, to generate image data, and further subjects the thus obtained multiple pieces of image data to synthesis processing, subtraction processing, etc. The image generation circuitry 6 is capable of generating desired X-ray images, for example, two-dimensional X-ray fluoroscopic images, three-dimensional digital subtraction angiography (DSA) images, three-dimensional low contrast imaging (LCI) images, and X-ray tomograms.

The display 7 includes a display main part for displaying medical images, etc., internal circuitry for supplying display signals to the display main part, and peripheral circuitry including connectors, cables, and the like for connection between the display main part and the internal circuitry. The internal circuitry generates display data by superimposing supplemental information, such as information about a subject and projection data generation conditions, onto the image data supplied from the image arithmetic circuitry of the image generation circuitry 6, subjects the generated display data to digital-analog conversion and TV format conversion, and displays the resultant data. The display 7 may also display an error message based on an error output received from the processing circuitry 23.

The mechanism driver 10 includes an imaging system movement mechanism driver 11, a couch top movement mechanism driver 12, and a mechanism driver controller 13. The imaging system movement mechanism driver 11 supplies drive signals to each movement mechanism installed at the holder 8 for moving the imaging system in desired directions. The couch top movement mechanism driver 12 supplies drive signals to the movement mechanism installed at the couch 9 for moving the couch top in a desired direction together with the subject 150 placed on the couch top. The mechanism driver controller 13 controls the imaging system movement mechanism driver 11 and the couch top movement mechanism driver 12. The mechanism driver controller 13 has a function of, for example, controlling the imaging system movement mechanism driver 11 based on control information supplied from the system control circuitry 26 so that the imaging system attached to the holding portion is moved or rotated.

Next, a description will be given with reference to FIG. 3, as to how the holder 8 and the couch 9 are structured and how the units constituting them move or rotate. The description will assume an X-ray diagnostic apparatus for circulatory organs that adopts a floor-standing type C-arm as the holding portion. However, this is not a limitation, and the holding portion may be, for example, a C-arm or a Q-arm that could hang from the ceiling. Also, the apparatus may be, for example, a general-purpose medical image diagnostic apparatus that can handle diagnoses for circulatory organs and digestive organs. FIG. 3 shows the holder 8, of which holding portion 81 is a C-arm adapted to carry the X-ray generator 2 and the X-ray detector 3 at the respective ends. The figure also shows the couch 9 including the couch top 91 on which the subject 150 is placed. To facilitate the understanding, the figure assumes that a direction along the body axis of the subject 150 (i.e., longitudinal direction of the couch top 91) represents a y-axis, a direction along the central axis (motion axis) of a stand 83 that holds the holding portion (C-arm) 81 represents a z-axis, and a direction perpendicular to both the y-axis and the z-axis represents an x-axis.

For the holding portion 81, the X-ray generator 2 is attached to one end and the X-ray detector 3 is attached to the other end so that they face each other. The holding portion 81 is held by the stand 83 via a holding portion holder 82. The holding portion 81 is attached to the side face of the holding portion holder 82 in such a manner that it can slide in the direction of an arrow (a). Note that the holding portion holder 82 is attached to the stand 83 in such a manner that it can rotate in the direction of an arrow (b). Thus, the holding portion 81 also rotates about the x-axis according to the rotation of the holding portion holder 82. Further, the imaging system member is attached to the end of the holding portion 81 in such a manner that it can slide in an (e) direction. Accordingly, with the slide movement of the holding portion 81 in the (a) direction, the rotation of the holding portion holder 82 in the (b) direction, and the slide movement of the imaging system member in the (e) direction, it is possible to set the imaging system attached to the holding portion 81 at any position or in any direction relative to the subject 150 placed on the couch top 91.

A floor swing arm 84 is installed on a floor face 160. One end of the floor swing arm 84 is attached to the floor face 160 in such a manner that the floor swing arm 84 can pivot about a motion axis z1, and the other end of the floor swing arm 84 is attached to the stand 83 and makes the stand 83 turnable about a motion axis z2. In this instance, both the motion axis z1 of the floor swing arm 84 and the motion axis z2 of the stand 83 are set along the z-axis.

That is, the position information of the imaging system is unambiguously determined by [i] to [v], which are: [i] a distance traveled by the holding portion 81 by the slide movement relative to the holding portion holder 82; [ii] an angle of the holding portion holder 82 formed by rotating in the (b) direction; [iii] an angle of the floor swing arm 84 formed by pivoting in the (d) direction; [iv] an angle of the stand 83 formed by turning in the (c) direction; and [v] a distance traveled by the imaging system by the slide movement relative to the holding portion 81.

Therefore, the position information of the imaging system can be obtained by detecting drive signals (for example, by counting the number of drive pulses) supplied from the imaging system movement mechanism driver 11 to the respective movement mechanisms of the holder 8 for the movement, rotation, etc. of the holding portion 81, the holding portion holder 82, the stand 83, and the floor swing arm 84 in given directions. The movement mechanisms here include a holding portion sliding mechanism for sliding the holding portion 81, a holding portion holder rotating mechanism for rotating the holding portion holder 82 in the (b) direction, a stand turning mechanism for turning the stand 83 in the (c) direction, a floor swing arm pivoting mechanism for causing the floor swing arm 84 to pivot in the (d) direction, and an imaging system sliding mechanism for sliding the imaging system in the (e) direction. Also, the couch 9 includes a couch body 92 with a horizontal movement mechanism for horizontally moving the couch top 91 in the body axis direction ((f) direction) and a vertical movement mechanism for vertically moving the couch top 91 in a (g) direction, together with the subject 150 placed on the couch top 91.

In this embodiment, the position information of the imaging system may be detected based on outputs of first encoders and second encoders, instead of using the drive signals. Each first encoder detects the rotation of a drive motor driven by the drive signals, and each second encoder detects the rotation of a motion axis on the load side. To supplement the description with reference to an example shown in FIG. 4, the rotation mechanism transmits the rotating force of a drive motor mtr to a motion axis e, via a power transmission mechanism that includes a first belt vlt1, a worm reducer wrg, a first timing belt pulley tvp1, a second belt vlt2, a second timing belt pulley tvp2, etc. In the example of FIG. 4, the X-ray detector 3 (not shown) will rotate about the motion axis e in accordance with the rotation of the motion axis e.

The rotation mechanism of this type incorporates a first encoder enc1 in the drive motor (servo motor) mtr disposed on the drive side. A second encoder (external encoder) enc2 is provided near the motion axis on the load side. Such a configuration to detect a rotation, turn, etc., using the drive-side and load-side encoders enc1 and enc2 is likewise applicable to all the motion axes. Taking the holding portion holder rotating mechanism as an example, it transmits the rotating force of the drive motor to the motion axis via the power transmission mechanism so that the holding portion holder 82 holding the holding portion 81 is rotated in the (b) direction. This holding portion holder rotating mechanism is also provided with the first encoder for detecting the rotation of the drive motor, and the second encoder for detecting the rotation of the motion axis. The first encoder outputs a first pulse signal having a pulse train based on the detection of the rotation of the drive motor. The first pulse signal is supplied to the position information detector 21 via the imaging system movement mechanism driver 11. The second encoder outputs a second pulse signal having a pulse train based on the detection of the rotation of the motion axis. The second pulse signal is supplied to the position information detector 21 via the imaging system movement mechanism driver 11.

The position information detector 21 receives the pulse signals from the respective movement mechanisms of the holder 8 via the imaging system movement mechanism driver 11, and detects the position information of the holding portion 81 and that of the imaging system attached to the holding portion 81 based on the pulse signals. The detected position information is written in the storage 22.

In order to detect the position information, the position information detector 21 includes first measurement circuitry 21a for measuring the pulse number given by each pulse signal, and second measurement circuitry 21b for measuring the rotation angle from each of the measured pulse numbers. The pulse numbers and the rotation angles correspond to the position information. The rotation angle is a value of angle converted from the pulse number, and constitutes the position information for the display 7 to display. The expressions such as "measure" and "measurement circuitry" may be replaced with other expressions, e.g., "detect" and "detection circuitry", respectively.

Figure 5:
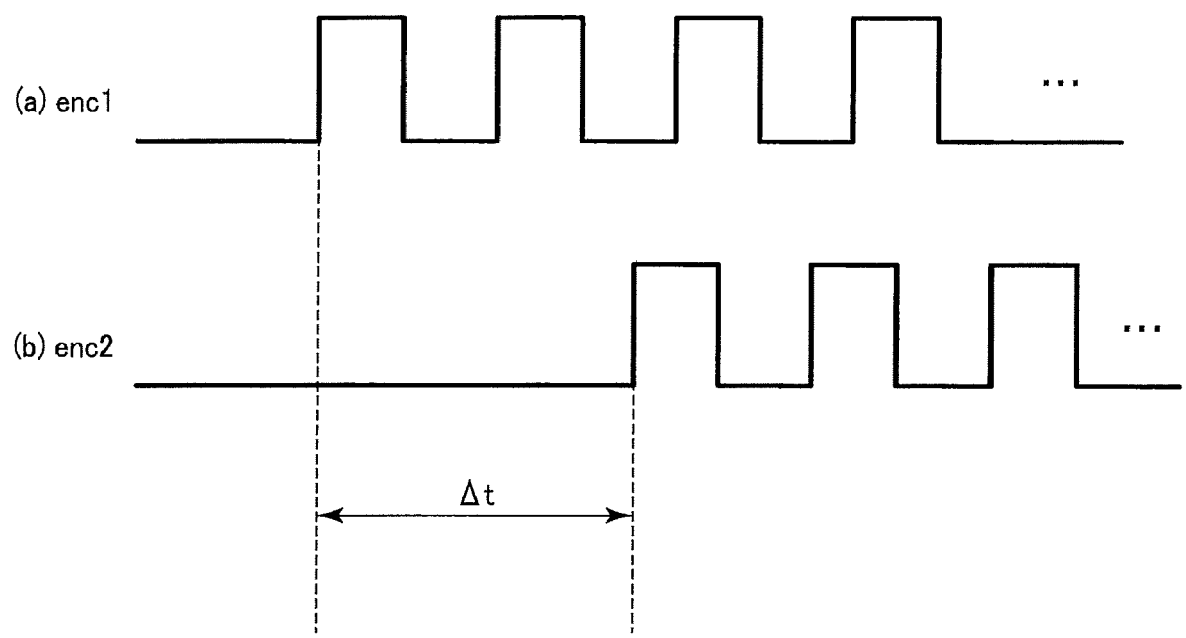
FIG. 5 is a waveform chart of pulse signals from respective encoders according to the embodiment.

FIGS. 5 (a) and (b) schematically show a time difference Δt between the leading pulse of the first pulse signal output from the first encoder enc1 and the leading pulse of the second pulse signal output from the second encoder enc2. It is desirable to have a small difference value for this time difference Δt, as the difference value is a counterpart of the degree of looseness and unsteadiness in the power transmission mechanism. The difference value corresponds to the difference between a first pulse number measured from the first pulse signal and a second pulse number measured from the second pulse signal, but may depend on a configuration of the power transmission mechanism between the drive motor and the motion axis. For example, supposing that the first pulse number according to the rotation of a drive motor is 10000, and the second pulse number according to the rotation of a motion axis is 9998, the difference value corresponds to 2 pulses that is a difference between the pulse numbers. If there is no unsteadiness in the mechanical system, the first pulse number and the second pulse number will show one-to-one correspondence.

The first measurement circuitry 21a and the second measurement circuitry 21b as such can be implemented by, for example, a ROM (not shown) storing programs, and a processor (not shown) executing the programs in the ROM.

The position information detector 21 further detects position information of the couch top 91 of the couch 9, based on the drive signals supplied from the couch top movement mechanism driver 12 to each movement mechanism of the couch 9.

The storage 22 includes a memory such as a hard disk drive (HDD) for storing electric information, and peripheral circuitry such as a memory controller and a memory interface that pertain to the memory. The storage 22 stores programs to be executed by the system control circuitry 26 and the processing circuitry 23, and various types of information written by the processing circuitry 23. As shown in FIG. 6, such various types of information include, for example, a log table 22a, an operating sound management table 22b, a normal sound management table 22c, various thresholds, an acceptable value, and so on. The operating sound management table 22b and the normal sound management table 22c are optional features and may be omitted.

The log table 22a is a table to store information items such as an apparatus ID, time, an operation, motion information (e.g., motion axis, position information, rotation number, and electric-current value), incident data (e.g., operating sound data and shaking data), and an error flag, in association with each other. Item "Apparatus ID" is an identifier that allows unique identification of the medical image diagnostic apparatus 100. Item "Time" is time information including a year, a month, a day, minutes, and seconds. Item "Operation" is information indicative of the contents of an operation on the input interface 25. The motion information is indicative of the working conditions of the medical image diagnostic apparatus 100 and includes items such as "Motion axis", "Position information" and "Rotation number" for each motion axis, and "Electric-current value" for each drive motor to rotate the motion axis. The "motion information" may be read as "information for motion". The electric-current values for the drive motors are measured by an ammeter (not shown) and stored in the log table 22a by the processing circuitry 23. The item "Motion axis" is an axis identifier for identification of the axis intended by the motion information. The item "Position information" includes a pulse number of the aforementioned encoders, and an angle converted from the pulse number. The angle may, however, be omitted. The item "Rotation number" is a count value that uses the angle converted from the pulse number in such a manner that each 360° is counted as one rotation. The items "Position information" and "Rotation number" each represent an example of the information for an amount of motion of the movable part. The incident data includes at least either of operating sound data or shaking data. The description of this embodiment will assume use of item "Operating sound data" as one example of the incident data. The item "Operating sound data" is digital data of the operating sounds generated by the mechanisms, and collected by a sound collector (not shown) and stored in the log table 22a by the processing circuitry 23. The sound collector may be attached to the medical image diagnostic apparatus 100 or may be arranged in an inspection room where the medical image diagnostic apparatus 100 is located. The shaking data is digital data of the shaking generated by the mechanisms, and may be collected by an acceleration sensor (not shown) and stored in the log table 22a by the processing circuitry 23. The acceleration sensor may be provided at a position of the holder 8 where the shaking of the mechanisms can be detected, and may be utilized for controlling the holder 8 to smoothly operate. As the aforementioned incident data, the shaking data collected by this acceleration sensor may be adopted as well, in order to detect an abnormality in the mechanisms. Item "Error flag" is a flag to indicate whether or not there is an error. When the error flag indicates an error, the log table 22a may further store item "Threshold" corresponding to the error.

The operating sound management table 22b is a table to store information items such as an apparatus ID, a particular motion pattern, a motion axis, position information, a rotation number, operating sound data, threshold for operating sound data, and a threshold for an amount of shift in frequency band, in association with each other. As described above, item "Operating sound data" is an example of the incident data here. The operating sound management table 22b as such may be adapted to pre-store, for example, the position information and the rotation number-to-operating sound relationship that correspond to a particular motion pattern, and can be used for an operation of transmitting the data to the server 300, operation of conducting a spectral analysis of the operating sound data, and so on, upon the operating sound in the corresponding motion pattern exceeding a threshold. If the shift amount in frequency band, obtained from the result of this spectral analysis, is smaller than the existing threshold for a shift amount, the existing threshold is updated to the value of the shift amount obtained from the spectral analysis, as appropriate by an operator's operation. Also, even if a malfunction is due to a known cause and repair is to be done, the operating sound management table 22b may be used for storing the operating sound data to accumulate abnormal sound data. These explanations for the operating sound data are likewise applicable to the shaking data by replacing "operating sound", "operating sound data", and "abnormal sound data" with "shaking", "shaking data", and "abnormal shaking data", respectively. As to items "Apparatus ID", "Motion axis", "Position information", "Rotation number", and "Operating sound data", they are as explained above. Item "Particular motion pattern" is identification information for the cases of, for example, the medical image diagnostic apparatus 100 operating on a fixed motion pattern such as the pattern in 3D-DSA or 3D-LCI, and is indicative of this motion pattern. Item "Threshold for operating sound data" is a maximum value (dB) of the normal operating sound, and is used for determining that an operating sound exceeding this value is an abnormal sound. Item "Threshold for shift amount in frequency band" is a maximum value of the amount of shift in frequency band between pre-stored normal operating sound data and operating sound data collected this time, and is used for determining that an operating sound exceeding this value is an abnormal sound.

The normal sound management table 22c is a table to store information items such as a motion pattern, a motion axis, a start position, a goal position, operating sound data, a motion speed, a first pulse number, and a second pulse number, in association with each other. Item "Motion pattern" is information to identify a pattern of the motion of the medical image diagnostic apparatus 100. Items "Motion axis" and "Operating sound data" are as explained above. Item "Start position" is information of the position of the motion axis at the start of the motion corresponding to the item "Motion pattern". Item "Goal position" is information of the position of the motion axis at the end of the motion corresponding to the item "Motion pattern". Item "Motion speed" indicates a speed during the motion corresponding to the item "Motion pattern". As the item "Motion speed", for example, an angular speed obtained by converting the pulse number measured per unit time into an angle (e.g., 50°/sec, 10°/sec, etc.) may be adopted. Item "First pulse number" is a pulse number measured from the first pulse signal that corresponds to the rotation of the drive motor. Item "Second pulse number" is a pulse number measured from the second pulse signal that corresponds to the rotation of the motion axis, and represents the position information between the "Start position" and the "Goal position". If the difference between the first pulse number and the second pulse number is larger than a threshold, there could be an abnormality in the mechanical system.

The various thresholds are values each indicative of a boundary between a normal range and an abnormal range. As these thresholds, for example, it is possible to adopt a threshold for pixel shift that is associated with an apparatus ID and a function, a threshold for motion time that is associated with an apparatus ID and a function, a threshold for an electric-current value that is associated with an apparatus ID and a motion axis, and so on, as appropriate. The pixel shift refers to an operation in which an image having been obtained by subjecting image data to synthesis processing, subtraction processing, etc., is corrected in units of pixels, if the image includes misalignment or artifacts. Here, the function associated with the threshold for pixel shift is, for example, a function of 3D-DSA. To supplement the description, a mechanical system would deteriorate the positioning accuracy and response characteristics when large unsteadiness is involved, causing 3D-DSA and 3D-LCI to produce artifacts. To address these artifacts, the pixel shift for correcting images is performed in the 3D-DSA. To put it another way, if a value of the pixel shift exceeds the set threshold, a mechanical system may likely involve an abnormality. That is, the threshold for pixel shift can be used as a parameter for detecting an abnormality in the mechanical systems. Note that, in the context of this embodiment, an abnormality in a mechanical system indicates an abnormality in a mechanism. For example, large unsteadiness in a mechanical system indicates large unsteadiness in a mechanism including a movable part.

Also, the function associated with the threshold for motion time is, for example, a function of 3D-DSA or a function of 3D-LCI. To supplement the description, particular motion patterns are defined for 3D-DSA, 3D-LCI, etc. As such, when a mechanical system involves large unsteadiness, the mechanical system degrades response characteristics such as motion time. The threshold for motion time can therefore be used as a parameter for detecting an abnormality in the mechanical systems.

Further, as to the motion axis associated with the threshold for an electric-current value, the electric-current value refers to an electric-current value for the drive motor to rotate the motion axis, and it tends to become excessive when the motion axis is difficult to move due to an increased mechanical resistance. Thus, the threshold for an electric-current value associated with the motion axis can be used as a parameter for detecting an abnormality in the mechanical systems. Electric-current values for the drive motors are measured by an ammeter (not shown).

The acceptable value is indicative of a normal range. As the acceptable value, for example, a value indicative of the acceptable range of a change in tube focus size may be adopted. To supplement the description, if a change in the tube focus size is measured using a phantom, and the measurement result exceeds the acceptable value, it is assumed that a mechanical system involves an abnormality. This is because, specifically, a change in tube focus size is due to the shift (shake) of a target axis supported by a bearing. When a target axis is being shifted, an abnormal sound is produced.

The acceptable value as such corresponds to the normal range delimited by the thresholds described above. To supplement the description, when a mechanism turns from a normal motion to an abnormal motion, respective information items representing the image analysis result, the motion, etc., transition from an acceptable value to a threshold, and then to an abnormal value. The relationship between the acceptable value and the threshold is that the limit of the acceptable value corresponds to the threshold. Thus, if both the acceptable value and the threshold enable abnormality detection, the acceptable value and the threshold may be replaced by each other as appropriate. For example, an expression "if an acceptable value is exceeded" may be replaced by "if a threshold is exceeded". Likewise, an expression "if a threshold is exceeded" may be replaced by "if an acceptable value is exceeded".

The processing circuitry 23 (first processor) is a processor that reads and executes processing programs in the storage 22 to realize an operating sound processing function 23a and a receive function 23b corresponding to the programs. The receive function 23b is an optional feature and may be omitted. It has been shown in FIG. 2 that the operating sound processing function 23a and the receive function 23b may be realized by single processing circuitry 23, but this disclosure is not a limitation. For example, multiple independent processors may be combined to form the processing circuitry 23 to have the respective processors run the programs, so that each function will be realized.

The operating sound processing function 23a generates a subject image based on the output of the X-ray imager 1, and processes the incident data containing at least either of the operating sound data or the shaking data of the mechanism based on at least either of the analysis result of the subject image or the information for motion of the mechanism. In this instance, the operating sound processing function 23a may carry out at least one of collecting, storing, transmitting, or analyzing the incident data, as the incident data processing. For this transmitting, the operating sound processing function 23a may also include a function of transmitting the incident data and the information for motion to the server 300 via the network interface 27. In the present embodiment, the "information for motion" is also called "motion information".

At least one of collecting, storing, or transmitting the incident data may be performed in the manner, for example, as described in each of below (A) to (D). The same is applicable to analyzing the incident data.

(A) In the case where the first pulse number and the second pulse number are used as the position information included in the motion information, the incident data is collected, stored, and transmitted if, as a trigger, the time difference Δt between the leading pulse of the first pulse train and the leading pulse of the second pulse train is larger than the threshold. That is, in this manner (A), the incident data is collected, stored, and transmitted based on the motion information. The collected incident data is written in a region of the storage 22 for a prescribed amount so that the older data is overwritten and updated as in the configuration of a drive recorder. Note that the write operation to the storage 22 here is different from the "storing" in "collecting, storing, or transmitting the incident data".

(B) The incident data is constantly collected, and the incident data is stored and transmitted if, as a trigger, the electric-current value shows an abnormality. That is, in this manner (B), the incident data is stored and transmitted based on the motion information.

(C) The incident data is constantly collected and stored, and the incident data is transmitted if, as a trigger, the result of analyzing an image indicate an abnormality. That is, in this manner (C), the incident data is transmitted based on the result of analyzing the image of a subject.

(D) The incident data is constantly collected and stored, and the incident data is transmitted if, as a trigger, a traveling time for a predetermined interval shows an abnormality. That is, in this manner (D), the incident data is transmitted based on the motion information.

Differing from these manners (A) to (D) which are based on the image analysis result or the motion information, the incident data itself can be referred to. In this case, the incident data is constantly collected, and the incident data is stored and transmitted if, as a trigger, the incident data shows an abnormality. That is, the incident data is stored and transmitted based on the incident data itself.

The analysis of the incident data can be performed likewise, upon the trigger as in each of the manners (A) to (D) or upon the trigger based on the abnormality in the incident data.

As the operating sound processing function 23a, for example, the operation given in any of the following (a) to (f) may be carried out.

(a) The motion information may contain an electric-current value for the motor for driving the mechanism. In this instance, the operating sound processing function 23a may collect the incident data and the motion information, and carries out the incident data processing upon the condition for the electric-current value becoming satisfied. For example, the operating sound processing function 23a stores and transmits the collected incident data upon the electric-current value exceeding the threshold. In another instance, the operating sound processing function 23a may analyze the collected incident data upon the electric-current value exceeding the threshold.

(b) If a subject image contains, as supplementary information, a value of the pixel shift for correcting misalignment in the image, the operating sound processing function 23a collects and stores the incident data and the motion information, and transmits the stored incident data if the value of the pixel shift is equal to or greater than the acceptable value.

(c) If the motion information contains a traveling time for the imaging unit to move by a predetermined interval, the operating sound processing function 23a collects and stores the incident data and the motion information, and transmits the stored incident data and motion information upon the conditions for the traveling time becoming satisfied. For example, the operating sound processing function 23a transmits the stored incident data and motion data upon the traveling time exceeding the threshold.

(d) The operating sound processing function 23a performs the transmission according to a result of comparing the collected incident data and the threshold.

(e) The operating sound processing function 23a specifies a position gap between images, and carries out the incident data processing upon the condition for the position gap becoming satisfied. For example, the operating sound processing function 23a carries out the incident data processing if the size of the position gap is equal to or greater than the acceptable value.

(f) The operating sound processing function 23a performs image reconstruction using multiple images taken, and carries out the incident data processing upon the condition for an artifact in the reconstructed image becoming satisfied. For example, the operating sound processing function 23a carries out the incident data processing upon detection of an artifact in the reconstructed image.

The operating sound processing function 23a may separately output an error indication at the time of transmitting the incident data, etc., to the server 300. The output of an error indication may be supplied to, for example, the display 7, the alarm generator 24, and the system control circuitry 26.

The operating sound processing function 23a may also output the information from the network interface 27 to the server 300 via the network Nw, which may be the Internet lines, using a remote maintenance system such as InnerVision®. In this case, engineers of the apparatus manufacturer can start a maintenance operation upon receipt of a communication from the server 300 in accordance with a result of determination, so that maintenance can be performed efficiently.

The receive function 23b is a function to receive, from the server 300, maintenance management information associated with the incident data and the motion information that have been transmitted by the operating sound processing function 23a.

The alarm generator 24 includes, for example, a buzzer or a speaker (now shown), and generates an alarm sound based on the error output received from the processing circuitry 23.

The input interface 25 is realized by elements that allow for setting a region of interest (ROI), etc., such as a trackball, switch buttons, a mouse, a keyboard, a touch pad which allows an input operation through contacting the operation screen, a touch panel display which integrates a display screen and a touch pad, and so on. The input interface 25 is connected to the system control circuitry 26. The input interface 25 converts input operations received from operators into electric signals, and outputs the electric signals to the system control circuitry 26. In the present disclosure, the input interface 25 is not limited to physical operation components such as a mouse and a keyboard. Examples of the input interface 25 may also include processing circuitry for electrical signals that receives an electrical signal corresponding to an input operation from an external input device separate from the apparatus, and outputs the electrical signal to the system control circuitry 26.

The system control circuitry 26 includes a processor and a memory (not shown), and various types of information entered or set by the input interface 25 are stored in the memory. The processor, based on such input information and setting information, takes total control over each unit of the medical image diagnostic apparatus 100 to perform safe and efficient X-ray imaging for the subject 150. The system control circuitry 26 may be furnished with a function of terminating the X-ray imaging based on the error output received from the processing circuitry 23.

The network interface 27 is circuitry for connecting the medical image diagnostic apparatus 100 to the network Nw for communications with the server 300. As the network interface 27, for example, a network interface card (NIC) may be adopted. In the following disclosure, such a description as the network interface 27 being present between the medical image diagnostic apparatus 100 and the server 300 for communication will be omitted.

Turning to the server 300, it includes a storage 31, processing circuitry 32, and a network interface 33.

The storage 31 includes a memory such as a hard disk drive (HDD) for storing electric information, and peripheral circuitry such as a memory controller and a memory interface that pertain to the memory. The storage 31 stores programs to be executed by the processing circuitry 32, and various types of information written by the processing circuitry 32. As shown in FIG. 8, such various types of information include, for example, a history table 31a, an operating sound management table 31b, various thresholds, an acceptable value, and so on. The operating sound management table 31b, the various thresholds, and the acceptable value are stored in the storage 31 so that if an instruction to update a threshold relate to pre- and post-update thresholds, the processing circuitry 32 may refer to the pre-update threshold. The operating sound management table 31b, the various thresholds, and the acceptable value within the storage 31 are optional features and may be omitted.

The history table 31a is a table to store past incident data, past information for motion, and past maintenance management information for mechanisms, in association with each other. For example, the history table 31a is a table to store information items such as an apparatus ID, time, an operation, maintenance management information (e.g., error name, error cause, and component to be replaced), motion information (e.g., motion axis, position information, rotation number, and electric-current value), operating sound data, a threshold, and an error flag, in association with each other. Items "Apparatus ID", "Time", "Operation", the motion information ("Motion axis", "Position information", "Rotation number", "Electric-current value"), "Operating sound data", and "Error flag" are as explained above. Item "Threshold" is a threshold that, when the error flag indicates an error, has been used for detecting the error. The maintenance management information includes, for example, cause of an error and a component to be replaced for each error name. Item "Error name" is a name related to the operating sound data or the motion data that has involved an error. As the item "Error name", it is possible to discretionarily use, for example, "Operating sound error" for an excessive operating sound, "Electric-current error" for an overcurrent, "Image misalignment" for an excess pixel shift value, "Motion time error" for a delayed motion time, "Tube focus size error" for an excessive change in tube focus size, and so on. Item "Error cause" is information indicative of the cause of an error, and may appropriately adopt, for example, "Chain slack", "Increased unsteadiness", etc. The unsteadiness represents a behavior caused due to looseness, play, or a void in mechanisms, and the possible factors are, for example, a backlash for a bearing and a gear, or an axis configuration. Item "Replacement component" is information indicative of a component that should be replaced for resolving an error. Note that it is not an absolute requisite to replace the component indicated by the item "Replacement component". For example, if the item "Replacement component" indicates a model number of a chain, while it is expected that an error in the mechanical system can be resolved by adjusting the slackness of the chain of this model number, the chain does not need to be replaced. As such, the "Replacement component" may be changed to a term that does not necessarily mean replacement, such as "Error solution information" or "Error causing component".

The operating sound management table 31b is a table to store information items such as an apparatus ID, a particular motion pattern, a motion axis, position information, a rotation number, operating sound data, a threshold for operating sound data, and a threshold for a shift amount in frequency band, in association with each other. Items "Apparatus ID", "Particular motion pattern", "Motion axis", "Position information", "Rotation number", "Operating sound data", "Threshold for operating sound data", and "Threshold for shift amount in frequency band" are as explained above.

As these thresholds, for example, it is possible to adopt as appropriate a threshold for pixel shift that is associated with an apparatus ID and a function, a threshold for motion time that is associated with an apparatus ID and a function, a threshold for an electric-current value that is associated with an apparatus ID and a motion axis, and so on. The respective thresholds are as explained above.

As the acceptable value, for example, a value indicative of the acceptable range of a change in tube focus size may be adopted. This acceptable value is as explained above.

Figure 7:
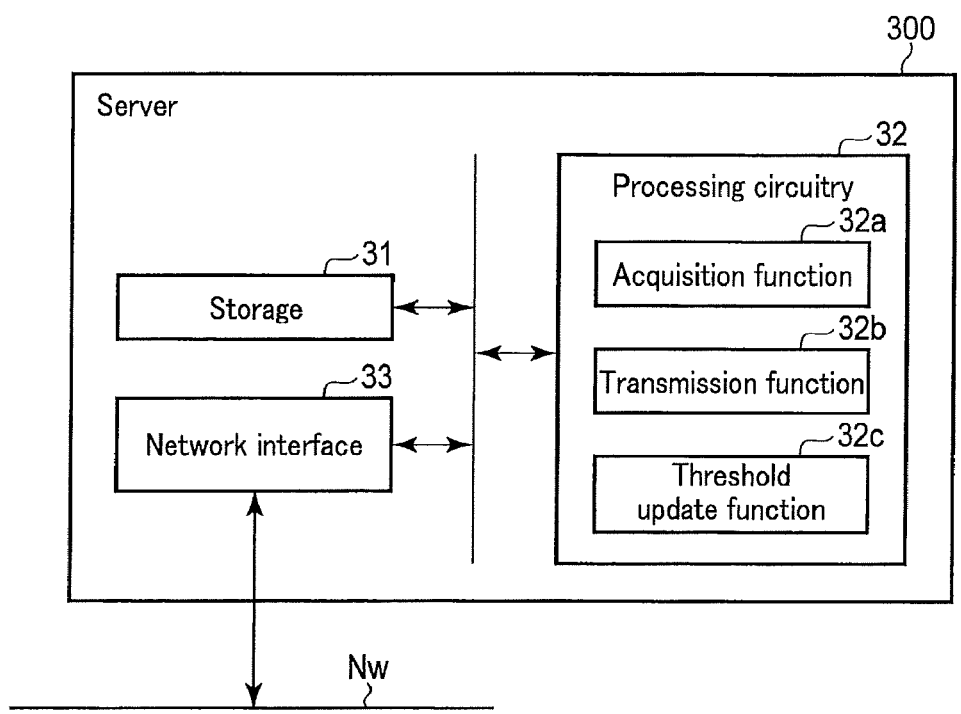
FIG. 7 is a schematic diagram showing a configuration of a server according to the embodiment.

The processing circuitry 32 (second processor) is a processor that reads and executes programs in the storage 31 to realize an acquisition function 32a, a transmission function 32b, and a threshold update function 32c corresponding to the programs. The threshold update function 32c is an optional feature and may be omitted. Also, while it has been shown in FIG. 7 that the acquisition function 32a, the transmission function 32b, and the threshold update function 32c are realized by single processing circuitry 32, this disclosure is not a limitation. For example, multiple independent processors may be combined to form the processing circuitry 32 to have the respective processors run the programs, so that each function will be realized.

The acquisition function 32a here is a function to acquire, in response to receiving the incident data and the information for motion (motion information) from the medical image diagnostic apparatus 100, maintenance management information for the received incident data and information for motion. For example, the acquisition function 32a may obtain from the storage 31 the maintenance management information associated with the incident data and the motion information which have been transmitted from the medical image diagnostic apparatus 100. In this context, the acquisition function 32a may include a verification function and a read function. The verification function is a function to check the incident data and the information for motion, received from the medical image diagnostic apparatus 100, against the past incident data and the past information for motion within the storage 31. The read function is a function to read and obtain, if the result of verification by the verification function has revealed the presence of the past incident data and information for motion that substantially conform to the received incident data and information for motion, maintenance management information associated with such substantially conforming past incident data and information for motion from the storage 31. The acquisition function 32a reads the maintenance management information from the storage 31 that stores maintenance management information for past data, but not only this, the acquisition function 32a may employ artificial intelligence (AI) to acquire the maintenance management information.

The transmission function 32b is a function to transmit the maintenance management information acquired by the acquisition function 32a to the medical image diagnostic apparatus 100 via the network interface 33.

The threshold update function 32c is a function to transmit, if the result of verification by the verification function has revealed that there is no past incident data or information for motion that substantially conforms to the received incident data or information for motion, a threshold update instruction for updating the threshold to the medical image diagnostic apparatus 100 via the network interface 33. The threshold that can be adopted here may represent, for example, a criterion for the medical image diagnostic apparatus 100 to determine whether or not the incident data should be transmitted to the server 300.

The network interface 33 is circuitry for connecting the server 300 to the network Nw for communications with the medical image diagnostic apparatus 100. As the network interface 33, for example, a network interface card (NIC) may be adopted. In the following disclosure, such a description as the network interface 33 being present between the server 300 and the medical image diagnostic apparatus 100 for communication will be omitted.

Now, the operations of the medical image diagnostic apparatus configured as above will be described with reference to the flowcharts in FIGS. 9 to 13.

Figure 9:
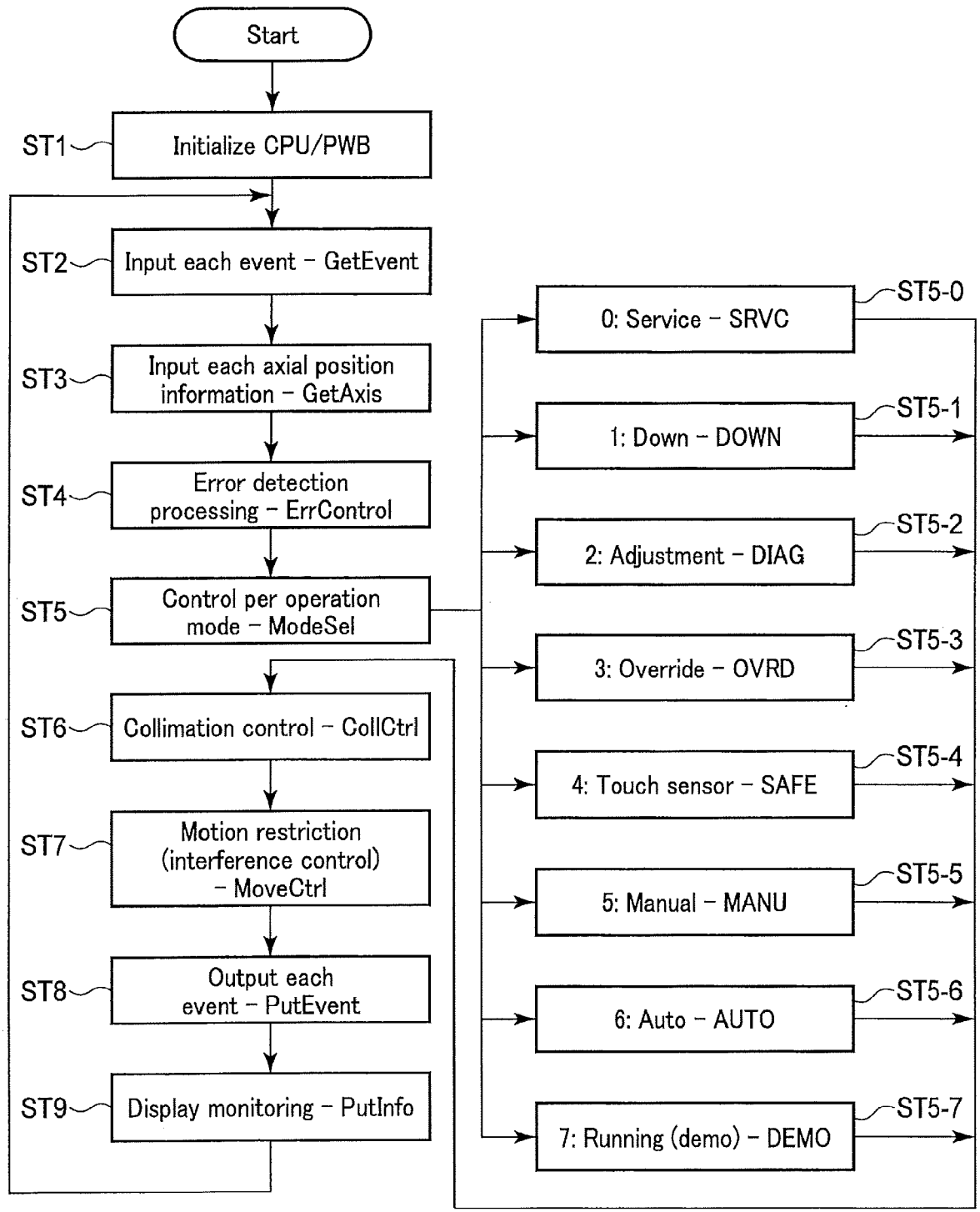
FIG. 9 is a flowchart for explaining general operations of the medical image diagnostic apparatus according to the embodiment.
Figure 11:
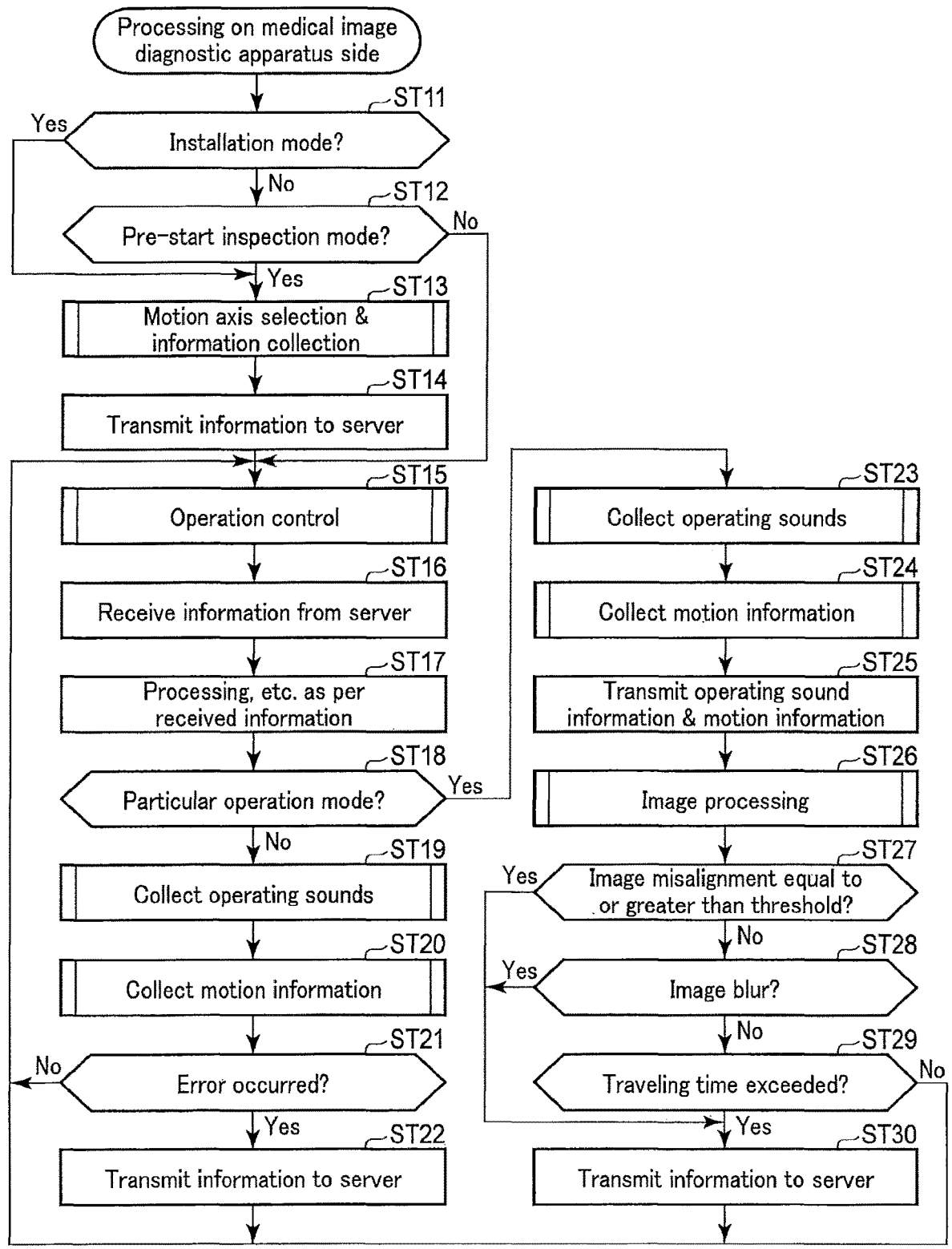
FIG. 11 is a flowchart for explaining operations of the medical image diagnostic apparatus according to the embodiment, for the processing for operating sounds.
Figure 12:
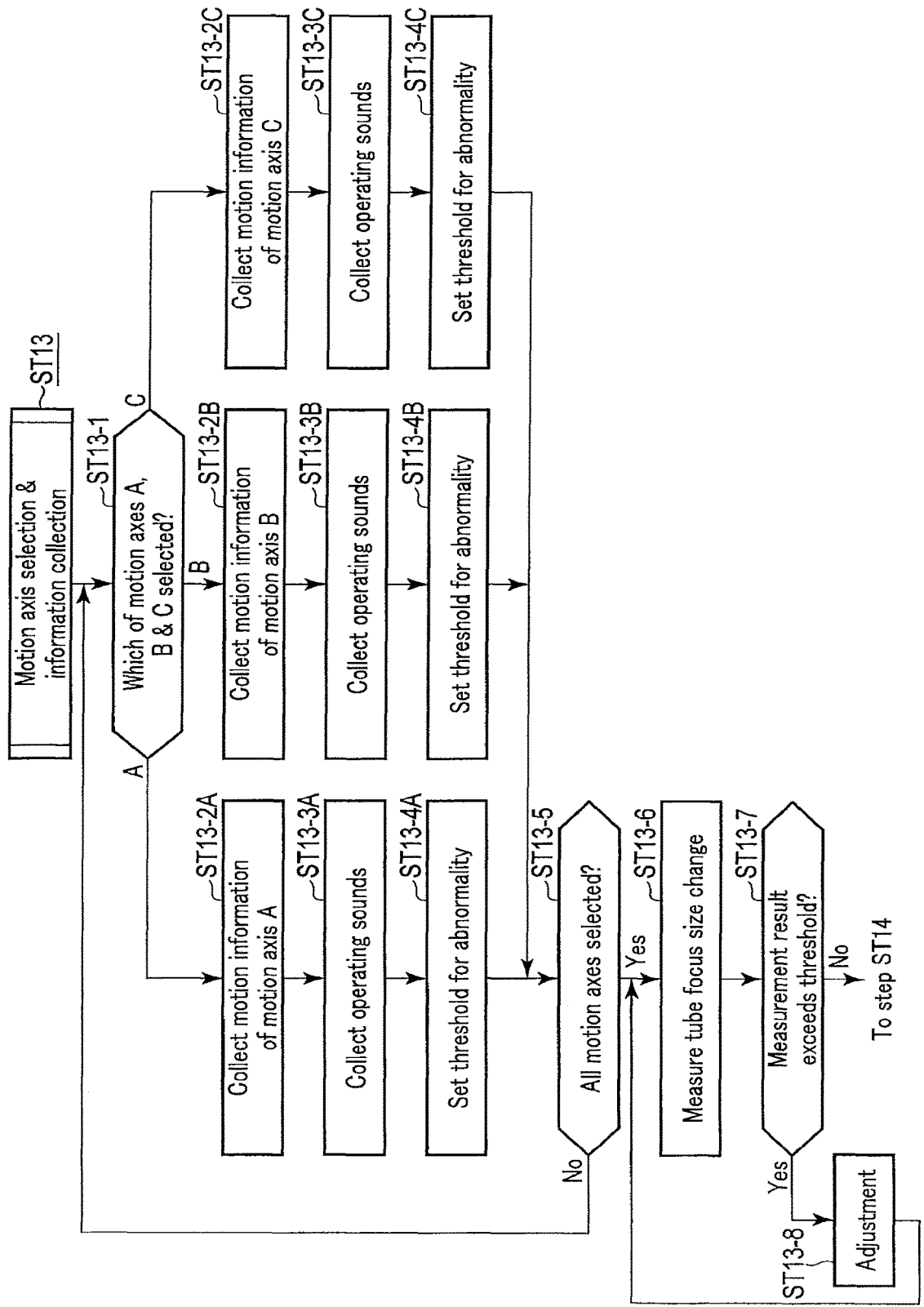
FIG. 12 is a flowchart for explaining operations for pre-start inspection according to the embodiment.

The following description will be directed to [General operations: FIG. 9], [Operations under adjustment mode: FIG. 10], and [Operations for operating sound processing and pre-start inspection, etc.: FIGS. 11 and 12] for the medical image diagnostic apparatus. Thereafter, the server 300 will be described with reference to FIG. 13. As stated above, the incident data will be described using the operating sound data as an example. For the instances where the incident data is shaking data, "operating sound" and "operating sound data" appearing in the following description may be read as "shaking" or "shaking data" as appropriate. Likewise, where the incident data is a combination of the operating sound data and the shaking data, "operating sound" and "operating sound data" below may be read as "operating sound and shaking" or "operating sound data and shaking data" as appropriate. The descriptions will be given one after another.

[General Operations: FIG. 9]

As per operations by an operator, the medical image diagnostic apparatus 100, as shown in FIG. 9, initializes a central processing unit (CPU) or a printed wired board (PWB) (step ST1) and then repeats steps ST2 to ST9.

Specifically, after step ST1, processing steps such as input of an event—GetEvent (step ST2), input of each axial position information—GetAxis (step ST3), error detection processing—ErrControl (step ST4), control per operation mode—ModeSel (step ST5), collimation control—CollCtrl (step ST6), motion restriction (interference control)—MoveCtrl (step ST7), output of each event—PutEvent (step ST8), and display of monitoring—PutInfo (step ST9) are repeatedly performed.

Also, the operation modes in step ST5 include a service mode—SRVC (step ST5-0), a down mode—DOWN (step ST5-1), an adjustment mode—DIAG (step ST5-2), an override mode—OVRD (step ST5-3), a touch sensor mode—SAFE (step ST5-4), a manual mode—MANU (step ST5-5), an auto mode—AUTO (step ST5-6), and a running (demo) mode—DEMO (step ST5-7).

The service mode for step ST5-0 is a mode for use by a service staff (hereinafter, "service engineer").

The down mode for step ST5-1 is a mode for operating under fallback conditions. For example, when there is an error, the down mode causes the axis involving the error to reduce its motion speed to a safe level, or to halt, while allowing the other axes to operate. This is because stopping all the axes would necessitate a catheter, etc. inserted into a subject to be blindly pulled out, and it is accordingly preferred to continue the inspection in even a limited manner.

Transition to this down mode may be done upon occurrence of an error under another mode, e.g., the auto mode or the manual mode. The down mode may also decelerate or stop, for example, operations applicable to the motion axis involving an error while permitting operations applicable to the other axes.

The adjustment mode for step ST5-2 is a mode for use at the time of check or adjustment, and serves for the adjustment of a backlash, etc. Under this adjustment mode, for example, a service engineer adjusts mechanical systems so that operating sounds produced by the mechanical systems in their normal state are collected.

The override mode for step ST5-3 is a mode for using override switches at a console to slowly move the holding portion 81 that has entered an interference region and stopped there, with an alarm sound generated.

The touch sensor mode for step ST5-4 is a special mode for use in the instance where a touch safety switch provided at the X-ray generator 2, the X-ray detector 3, or the holding portion 81 is touched and a detection signal is being output. In that instance, the motion axis of the related component is stopped, or an automatic movement for separation from the motion axis is invoked.

The manual mode for step ST5-5 is a mode for an operator to use an operation lever to cause the holding portion 81, etc., to move as a radio-controlled unit.

The auto mode for step S5-6 is a mode for operations that are performed according to programs in a memory upon selection of a number. Under this auto mode, for example, X-ray imaging is executed according to a selected given imaging sequence.

The running (demo) mode for step ST5-7 is a mode for predetermined operations that are performed for demonstration purposes.

During each of the above modes, for example, the auto mode for X-ray imaging according to a predetermined imaging sequence, or the manual mode for operations according to an operator's manipulation, the operating sound processing function 23a of the processing circuitry 23 performs at least one of collection, storage, transmission, or analysis of the operating sound data. This will be described in more detail later, with reference to FIG. 11.

[Operations Under Adjustment Mode: FIG. 10]

Next, operations under the adjustment mode in step ST5-2 will be described.

As per an operation of a service engineer, the input interface 25 of the medical image diagnostic apparatus 100 reads a motion pattern and puts it in the normal sound management table 22c in the storage 22 (step ST5-2a).

As per an operation of the service engineer, the input interface 25 inputs a start position (position information) of each motion axis for that motion pattern, in the normal sound management table 22c (step ST5-2b). The input start position may be an angle of the motion axis. The system control circuitry 26 converts the angle of the motion axis into a pulse number for control.

Subsequently, as per an operation of the service engineer, the input interface 25 sets a goal position of each motion axis for the motion pattern, in the normal sound management table 22c (step ST5-2c). The set goal position may be an angle of the motion axis. The system control circuitry 26 converts the angle of the motion axis into a pulse number for control.

Thereafter, the operating sound processing function 23a of the processing circuitry 23 controls motions of each motion axis from the start position to the goal position via the system control circuitry 26 (step ST5-2d). This control is performed for each motion axis. At this time, the first encoder, which is also called an internal encoder, detects the rotation of the drive motor driven by drive signals, and inputs the first pulse signal having a pulse train corresponding to the detection result into the position information detector 21 via the imaging system movement mechanism driver 11. Meanwhile, the second encoder, which is also called a load encoder, detects the rotation of the motion axis on the load side, and inputs the second pulse signal having a pulse train corresponding to the detection result into the position information detector 21 via the imaging system movement mechanism driver 11. The position information detector 21 measures the first pulse number from the first pulse signal and the second pulse number from the second pulse signal, and writes the measurement results in the normal sound management table 22c. The operating sound processing function 23a calculates a motion speed based on the second pulse number and writes it in the normal sound management table 22c. In this instance, if the difference between the first pulse number and the second pulse number is greater than the threshold, it may be recognized that the mechanical system involves increased unsteadiness, and as such, the followability of motor operations has been deteriorated and accurate positioning is hampered. Accordingly, the service engineer adjusts the mechanical system for the motion axis concerned, and then step ST5-2d is performed again. In this manner, the mechanical system for the motion axis is adjusted to be in the normal state where the difference between the first pulse number and the second pulse number is equal to or smaller than the threshold.

After completing step ST5-2d, the operating sound processing function 23a collects the operating sound data of the motion axis, with the normal-state mechanical system for the motion axis (step ST5-2e).

The operations in these steps ST5-2a to ST5-2e are repeated until collecting the operating sounds of each motion axis for all the intended motion patterns.

[Operations for Operating Sound Processing and Pre-Start Inspection, Etc.: FIGS. 11 and 12]

As shown in FIG. 11, under an installation mode or a pre-start inspection mode (step ST11/ST12: Yes), the medical image diagnostic apparatus 100 performs operations of motion axis selection and data collection in step ST13. If neither the installation mode nor the pre-start inspection mode is active, the processing flow advances to step ST15.

In step ST13, the medical image diagnostic apparatus 100 selects, for example, one of motion axes A to C as shown in FIG. 12 (step ST13-1). An example will be given, assuming that the motion axis A has been selected.

For the motion axis A, the processing circuitry 23 collects motion information such as position information, a rotation number, and an electric-current value (step ST13-2A), and also collects operating sound data (step ST13-3A). The processing circuitry 23 stores the operating sound data and the motion information, as well as the time, in the log table 22a. The input interface 25 sets a threshold for an abnormality in the storage 22, according to an operator's operation (step ST13-4A).

In step ST13-5, it is determined whether or not all the motion axes have been selected, based on the log table 22a (step ST13-5). If all the motion axes A, B, and C have been selected, the processing flow advances to step ST13-6. Otherwise, it returns to step ST13-1. Accordingly, steps ST13-2B to ST13-4B for the motion axis B, and steps ST13-2C to ST13-4C for the motion axis C are sequentially performed in the same manner as steps ST13-2A to ST13-4A as described.

Next, in step ST13-6, a change in tube focus size of the X-ray generator 2 is measured if a phantom used in the installation mode or the pre-start inspection mode is irradiated with X-rays. In parallel with this measurement, the operating sound data generated due to the rotation of a target axis supported by a bearing is collected, and the time, the operating sound data, and the motion information are stored in the log table 22a in the manner similar to the above.

The processing circuitry 23 determines whether or not the measurement result exceeds the threshold in the storage (step ST13-7). If the measurement result exceeds the threshold, the processing circuitry 23 sends an error output to the display 7 and the alarm generator 24. The display 7 and the alarm generator 24 thus output an error message and an alarm sound, respectively, so that a service engineer is prompted for the adjustment of the mechanical system of the X-ray generator 2. The service engineer, in consideration of suppressing a change in tube focus size, adjusts the mechanical system of the X-ray generator 2 so that the shaking of the target axis supported by the bearing is reduced. After that, upon the mechanical system having been adjusted (step ST13-8), the medical image diagnostic apparatus 100 returns to step ST13-6 to continue operations.

If, in step ST13-7, the determination result shows no, the processing circuitry 23 transitions to step ST14. The processing in step ST13, shown in FIG. 12, is thus completed.

After step ST13, the operating sound processing function 23a of the processing circuitry 23 transmits the information collected in step ST13 to the server 300 (step ST14). More specifically, among the information in the log table 22a, the operating sound processing function 23a transmits the information stored this time, together with the apparatus ID. The description about the operations of the server 300 will be provided later with reference to FIG. 13.

After step ST14, the processing circuitry 23 and the system control circuitry 26 control the medical image diagnostic apparatus 100 to perform operations for X-ray imaging of the subject 150 and to detect an error in the mechanical systems (steps ST15 to ST30).

At the timing that is, for example, prior to the X-ray imaging of the subject 150, an operator of the medical image diagnostic apparatus 100 inputs subject information or sets X-ray imaging conditions via the input interface 25. Moreover, the operator uses the input interface 25 to cause the imaging system attached to the holding portion (C-arm) 81 of the holder 8, and the couch top 91 of the couch 9 carrying the subject 150 thereon, to move/rotate to predetermined positions (initial positions).

At this time, the position information detector 21 detects the initial position information of the couch top 91 based on the drive signals that are supplied from the couch top movement mechanism driver 12 of the mechanism driver 10 to the horizontal movement mechanism and the vertical movement mechanism of the couch 9 when the couch top 91 and the imaging system move/rotate as above.

On the other hand, the drive motors for the holding portion 81 and the imaging system attached to this holding portion 81 rotate based on the drive signals supplied from the imaging system movement mechanism driver 11 to each of the holding portion sliding mechanism, the holding portion holder rotating mechanism, the stand turning mechanism, the floor swing arm pivoting mechanism, and the imaging system sliding mechanism of the holder 8. Each mechanism for rotation, etc., transmits the rotating force of the drive motor to the motion axis via the power transmission mechanism so that the holder 8 is rotated, etc. Likewise, the sliding mechanisms transmit the rotating force of the drive motor via the power transmission mechanisms, for the sliding movements of the holding portion 81 or the imaging system.

Also, the rotating mechanisms, etc., of the holder 8 each supply the first pulse signal that has been output from the first encoder for detecting the rotation of the drive motor, and the second pulse signal that has been output from the second encoder for detecting the rotation of the motion axis on the load side, to the position information detector 21 via the imaging system movement mechanism driver 11.

The position information detector 21 detects the initial position information based on the supplied first pulse signal and second pulse signal. Similarly, the position information detector 21 detects the position information of the holding portion 81 and the imaging system during their movement based on the first pulse signal and the second pulse signal supplied from the imaging system movement mechanism driver 11 according to the movement of the imaging system and based on the initial position information of the holding portion 81 and the imaging system.

Next, the operator starts X-ray fluoroscopy for the subject 150 by inputting a start command for the same, at the input interface 25. At this time, the medical image diagnostic apparatus 100 moves the imaging system toward a desired position, while the fluoroscopic image data generated by the X-ray imager 1 and the image generation circuitry 6 are being observed.

Next, slow movement/rotation of the imaging system is performed with the X-ray fluoroscopic image data being observed. Upon the imaging system having been set at the desired position for the subject 150, a command signal for stopping the movement/rotation of the imaging system, and a command signal for starting the X-ray imaging are input from the input interface 25.

Then, the system control circuitry 26 in receipt of these command signals controls the operations of the medical image diagnostic apparatus 100 so that the X-ray imaging based on predetermined X-ray imaging conditions is performed for the subject 150 (step ST15).

During such X-ray fluoroscopy and X-ray imaging, too, the operating sound data and the motion information that accompany the motions of the holder 8 are collected and the log table 22a is updated, as will be described in relation to steps ST19 to ST20 or steps ST23 to ST24.

Note that, among the operations in steps ST15 to ST30, steps ST15 to ST22 may be repeated so that an error in the mechanical system can be detected in real time if a particular operation mode is not active. The real time here means a certain short duration. A particular operation mode being not active means, for example, that one of the operation modes for step ST5 except the auto mode is active. In other words, the particular operation mode may indicate, for example, the auto mode for step ST5-6. Also, repeating the sequence of steps ST15 to ST18 and ST23 to ST30 enables the detection of an error in the mechanical system after generation of images of the subject, when a particular operation mode is active. Description will be given in the order of the step numbers.

It will be supposed that the processing circuitry 23 has received information from the server 300 (step ST16) after the transmission to the server 300 in step ST14, ST22, ST25, or ST30. In step ST16, the information received may be, for example, the maintenance management information containing an error name, an error cause, and a replacement component, or may be the threshold update instruction for instructing update of the threshold.

The medical image diagnostic apparatus 100 carries out processing according to the information received from the server 300 (step ST17). For example, when in receipt of the maintenance management information, the medical image diagnostic apparatus 100 displays the maintenance management information on the display 7 and performs the processing to prompt a maintenance operation for the mechanical system. In another instance, for example, when in receipt of the threshold update instruction, the processing circuitry 23 performs the processing to update the threshold in the storage 22 based on the threshold update instruction. Accordingly, even if an error occurs at the value that is smaller than the threshold set by the service engineer, the threshold can be updated to a smaller value. For example, if an error appears in the operating sound data even at the electric-current value smaller than the preset threshold for an electric-current value, the threshold update instruction from the server 300 allows the threshold for an electric-current value to be updated to a smaller value. Thus, the threshold update instruction may be used when an error is detected based on one threshold so that the other thresholds will be updated.

Next, the processing circuitry 23 determines whether or not the ongoing operation of the medical image diagnostic apparatus 100 is under a particular operation mode (step ST18). If yes, the processing flow skips to step ST23.

If the determination result in step ST18 is no, the operating sound processing function 23a of the processing circuitry 23 collects the operating sounds of the mechanical system (step ST19). Together, the motion information such as the position information, the rotation number, and the electric-current value is collected (step ST20), and a region of the storage 22 is overwritten and updated with the time, the operating sound data, and the motion information.

In step ST21, the operating sound processing function 23a determines whether or not an error has occurred in the mechanical system by comparing the information about the motion axis and the electric-current value in the log table 22a with the information about the motion axis and the threshold for an electric-current value in the storage 22. In this instance, if a particular motion pattern is used while the particular operation mode is not selected, the operating sound processing function 23a compares the operating sound data collected in step ST19 with the threshold for operating sound data in the operating sound management table 22b so that it is further possible to determine whether or not an error has occurred in the mechanical system. If the determination result in step ST21 is no, a region of the storage 22 is overwritten and updated with an error flag "0" that indicates free of errors. Then, the processing flow returns to step ST15 so that steps ST15 to ST21 will be repeated.

On the other hand, if it is determined in step ST21 that an error has occurred in the mechanical system, the operating sound processing function 23a stores the information that has superseded old information after the overwrite and update processing between steps ST19 and ST21, as well as an error flag "1" indicating the presence of an error, in the log table 22a. Thereafter, the operating sound processing function 23a transmits the stored information and error flag, the threshold used for the error determination, and the apparatus ID to the server 300 (step ST22). Additionally, in the event of error occurrence, the operating sound processing function 23a may also analyze the operating sound data stored in the log table 22a. The operations of the server 300 will be described later with reference to FIG. 13.

If it is determined in step ST18 that a particular operation mode is active, the operating sound processing function 23a collects the operating sounds of the mechanical system (step ST23). Together, the motion information such as the position information, the rotation number, and the electric-current value is collected (step ST24), and the time, the operating sound data, and the motion information are stored in the log table 22a. Note that the operating sound processing function 23a may also determine whether or not an error has occurred by comparing the operating sound data collected in step ST23 with the threshold for operating sound data in the operating sound management table 22b, and store an error flag corresponding to this determination result in the log table 22a. Then, in the event of error occurrence, the operating sound processing function 23a transmits the information stored in the log table 22a in steps ST23 to ST24, the threshold used for the error determination, and the apparatus ID to the server 300 (step ST25). In the event of error occurrence, also, the operating sound processing function 23a may analyze the operating sound data stored in the log table 22a. Note, however, that the transmission in step ST25 is not performed if no error has occurred. The operations of the server 300 will be described later with reference to FIG. 13.

After step ST25, the image generation circuitry 6 carries out image processing to generate an image of the subject based on the output from the X-ray imager 1 as the imaging system (step ST26). This image processing includes the processing according to imaging functions, such as 3D-DSA and 3D-LCI. In this instance, for example, when a mechanical system involves large unsteadiness during 3D-DSA, the mechanical system deteriorates positioning accuracy and response characteristics, which in turn cause image displacement (image misalignment) between a mask image and a contrast image. As a result, an image artifact is produced and sharp images may not be obtained. To cope with this, the image generation circuitry 6 executes pixel shift for correcting the image, and adds a pixel shift value to the supplementary information of the corrected image. Accordingly, the image of the subject will contain a pixel shift value for correcting image misalignment as the supplementary information.

After step ST26, the operating sound processing function 23a determines whether or not the image misalignment (pixel shift value) is equal to or greater than the threshold (step ST27). If it is equal to or greater than the threshold, the processing flow skips to step ST30.

If the determination result in step ST27 is no, the processing circuitry 27 determines whether the image shows a blur (step ST28). If the image shows a blur, the processing flow skips to step ST30. The image showing a blur may be determined based on the frequency analysis of the image, or the operator may input an indication that the image shows a blur.

If the determination result in step ST28 is no, the operating sound processing function 23a performs step ST29. Step ST29 is processing intended for the motion information containing a traveling time for the imaging system to move by a predetermined interval. Specifically, the operating sound processing function 23a determines whether or not this traveling time has exceeded the threshold (step ST29). If not, the processing flow returns to step ST15.

On the other hand, if it is determined in step ST29 that the traveling time has exceeded the threshold, the operating sound processing function 23a transitions its operation to step ST30.

In step ST30, the operating sound processing function 23a stores the error flag "1" indicating the presence of an error in the log table 22a, and then transmits the information stored in the log table 22a between steps ST23 to ST30, the threshold used for the error determination, and the apparatus ID to the server 300. Also, in the event of error occurrence, the operating sound processing function 23a may also analyze the operating sound data stored in the log table 22a. After completing step ST30, the medical image diagnostic apparatus 100 moves to step ST15. The description will be given of the operations of the server 300, with reference to FIG. 13.

Figure 13:
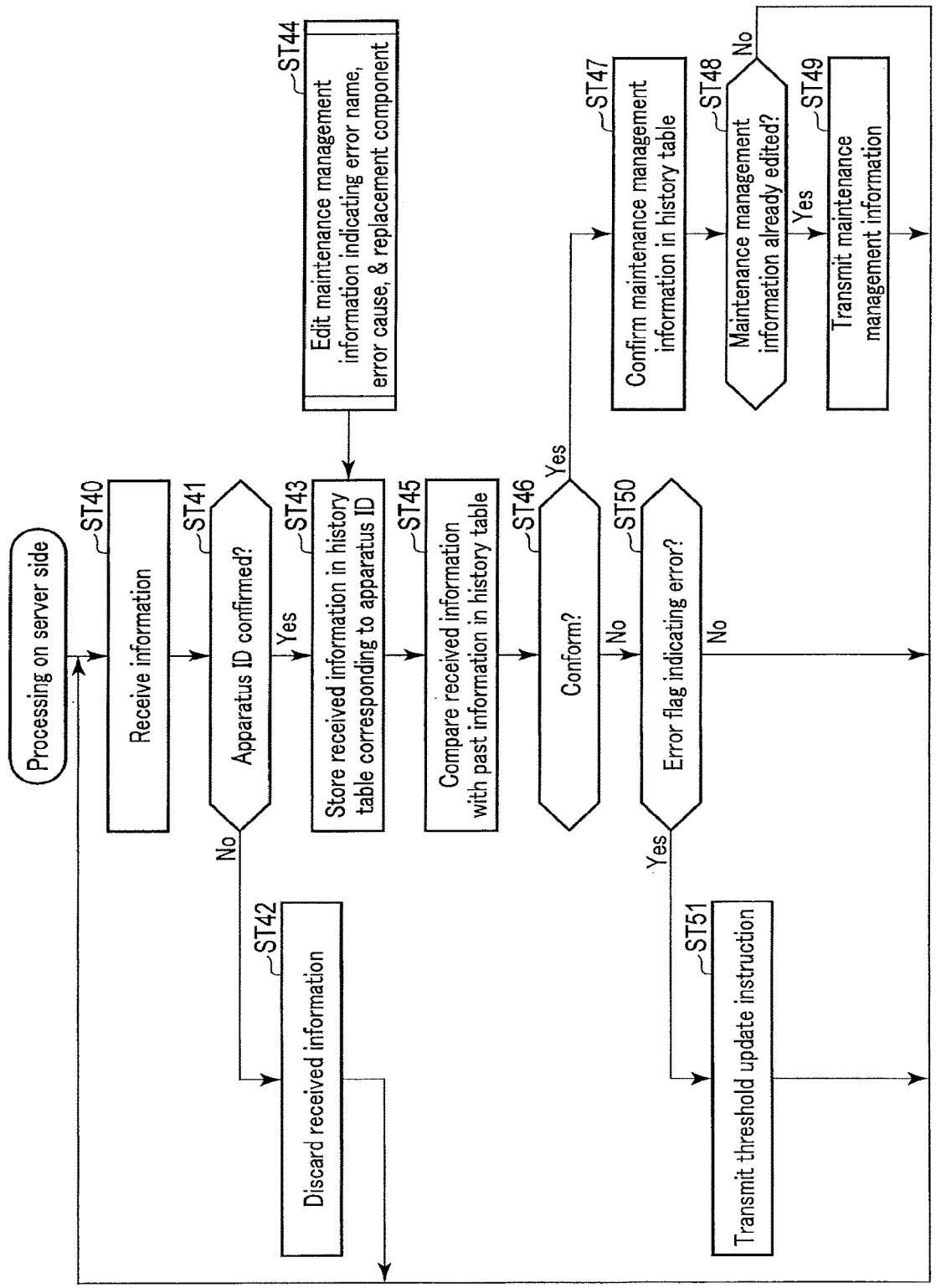
FIG. 13 is a flowchart for explaining operations of the server according to the embodiment.

[Operations of the Server 300: FIG. 13]

It will be supposed that the server 300 has received the information from the medical image diagnostic apparatus 100 after step ST14, ST22, ST25, or ST30 (step ST40). This received information contains, for example, the apparatus ID, the time, the operation, the motion axis, the position information, the rotation number, the electric-current value, the operating sound data, the threshold, and the error flag. Here, the item "Operation" is contained under, for example, the manual mode. The item "Threshold" is contained when, for example, an error has been determined.

The processing circuitry 32 of the server 300 determines whether or not the confirmation (detection) of the apparatus ID from the received information is possible (step ST41). If not, the processing circuitry 32 discards the received information (step ST42), and the processing flow returns to step ST40. Also, if the confirmation of the apparatus ID has been successful in step ST41, the received information is stored in the history table 31a that corresponds to the apparatus ID (step ST43). Note that this history table 31a is subject to regular or non-regular editing by a server administrator for the past information contents of the maintenance management information indicating error names, error causes, and replacement components (step ST44).

The acquisition function 32a of the processing circuitry 32 compares (verifies) the received information from the medical image diagnostic apparatus 100 with the past information in the history table 31a (step ST45), and determines whether or not they conform (or substantially conform) to each other (step ST46). More specifically, in step ST45, the operating sound data and motion information transmitted from the medical image diagnostic apparatus 100 are verified with the past operating sound data and motion information in the storage 31. In step ST46, it is determined whether or not there are past operating sound data and motion information that substantially conform to the transmitted operating sound data and motion information.

If it is determined in step ST46 that the received information contains the information substantially conforming to the past information, the acquisition function 32a confirms the maintenance management information associated with this past information within the history table 31a (step ST47).

After this confirmation, whether or not the maintenance management information has been edited in step ST44 is determined (step ST48). If not, the processing flow returns to step ST40. If, on the other hand, it is determined in step 48 that the maintenance management information has been edited, the acquisition function 32a acquires this maintenance management information by reading it from the storage 31.

The transmission function 32b of the processing circuitry 32 transmits the acquired maintenance management information to the medical image diagnostic apparatus 100 (step ST49). Thereafter, the processing flow returns to step ST40.

On the other hand, if the determination result in step ST46 is no (when there is no past operating sound data or motion information that substantially conforms to the transmitted operating sound data or motion information), the acquisition function 32a determines whether or not the error flag in the received information indicates an error (step ST50). If the determination result in step ST50 is no, the processing flow returns to step ST40. If it is determined in step ST50 that the error flag indicates an error, the threshold update instruction for updating the threshold is transmitted to the medical image diagnostic apparatus 100 (step ST51). Thereafter, the processing flow returns to step ST40.

As described above, the medical image diagnostic apparatus according to this embodiment generates a subject image based on the output of the imaging unit, and processes the incident data containing at least either of the operating sound data or the shaking data of a mechanism based on at least either of the analysis result of the subject image or the information for motion of the mechanism.

Therefore, unlike in the conventional techniques which required at least either of the operating sound data or the shaking data to be constantly processed, it is possible to reduce the data amount for processing, and realize efficient maintenance management.

Also, the processing circuitry may carry out at least one of collecting, storing, transmitting, or analyzing the incident data, as the incident data processing. For example, the processing circuitry may perform processing for analysis, in addition to the processing for the log (collection, storage, and transmission).

Moreover, if, for example, processing involves transmission, it is possible to reduce the amount of transmitted incident data and realize efficient maintenance management, unlike in the conventional techniques which required constant transmission of the incident data. Similarly, if processing involves analysis, the conventional techniques required constant analysis of the incident data; however, the embodiment can reduce the amount of analyzed incident data and realize efficient maintenance management. In addition to this, unlike in the conventional techniques which adopted monitoring only the incident data, it is possible to refer to at least an abnormality in either of the analysis result of a subject image or the information for motion, so that processing such as transmission of the incident data will be performed.

In the instance of this transmission, the information for motion may also be transmitted with the incident data. This enables the server 300 to use the information for motion as a verification subject when matching the received information with past information. Thus, the effect of facilitating the verification with past information may be expected.

Moreover, with the medical image diagnostic apparatus according to a certain embodiment, the information for motion may contain an electric-current value for a motor for driving a mechanism. In this case, when a mechanical resistance in the mechanism becomes large to make the mechanism difficult to move, an excessive electric-current value for the motor is detected. Therefore, an abnormality in the mechanism can be detected based on the information for motion. Also, in the event of such detection of an abnormality in the mechanism, the incident data processing can be performed.

In this instance, the processing circuitry collects the incident data and the information for motion, and may perform the incident data processing upon the condition for the electric-current value becoming satisfied. For example, when the electric-current value exceeds the threshold, the condition for the electric-current value is satisfied. This configuration enables the real-time detection of an abnormality in the mechanisms, independently of the incident data. Also, the processing to perform upon the condition for the electric-current value becoming satisfied may be, for example, storing and transmitting the incident data, or analyzing the incident data.

Also, the medical image diagnostic apparatus according to a certain embodiment collects and stores the incident data and the information for motion when a subject image contains a pixel shift value as supplementary information, and transmits the stored incident data and information for motion if the pixel shift value is equal to or greater than the acceptable value. This configuration enables the detection of an abnormality in the mechanisms after image generation, independently of the incident data.

Also, the processing circuitry may specify a position gap between images, and carry out the incident data processing upon the condition for the position gap becoming satisfied. This configuration enables the detection of an abnormality in the mechanisms after image generation, independently of the incident data.

Also, the processing circuitry may perform image reconstruction using multiple images taken, and carry out the incident data processing upon the condition for an artifact in the reconstructed image becoming satisfied. An abnormality in the mechanisms can therefore be detected after image generation, independently of the incident data.

Also, if the information for motion contains a traveling time for the imaging unit to move by a predetermined interval, the medical image diagnostic apparatus according to a certain embodiment may collect and store the incident data and the information for motion, and transmit the stored incident data and motion information upon the conditions for the traveling time becoming satisfied. For example, when the traveling time exceeds the threshold, the condition for the traveling time is satisfied. This configuration enables the detection of an abnormality in the mechanisms from the response characteristics such as motion time, independently of the incident data.

In the medical image diagnostic system according to a certain embodiment, the medical image diagnostic apparatus performs at least one of collecting, storing, or analyzing the incident data containing at least either of the operating sound data or the shaking data of a mechanism based on at least either of the analysis result of a subject image or the information for motion of the mechanism. When transmission is involved, the medical image diagnostic apparatus transmits the incident data and information for motion to the server. In response to the server having received the incident data and the information for motion from the medical image diagnostic apparatus, the maintenance management information associated with the received incident data and information for motion is obtained and transmitted to the medical image diagnostic apparatus.

Therefore, unlike in the conventional technique which required constant transmission and/or analysis of the incident data, it is possible to reduce the transmission amount and/or the analysis amount of the incident data, and realize efficient maintenance management. In addition to this, since the server transmits the relevant maintenance management information to the medical image diagnostic apparatus, further efficient maintenance management can be realized.

Also, any server in a server system may include the storage that stores past incident data and information for motion in association with the maintenance management information for the mechanisms. The processing circuitry of the server or servers may acquire the maintenance management information associated with the received incident data and information for motion, from the storage. At this time, the maintenance management information utilized in the past can be acquired from the storage based on the current incident data and information for motion.

Also, in the medical image diagnostic system according to a certain embodiment, when this acquisition of the maintenance management information is performed in the server, the received incident data and information for motion may be verified with the past incident data and information for motion in the storage. If the verification result has revealed the presence of the past incident data and information for motion that substantially conform to the received incident data and information for motion, the maintenance management information associated with these substantially conforming past incident data and information for motion may be read and acquired from the storage. This configuration can facilitate verification procedures as compared to the verification using only the incident data.

Also, in the medical image diagnostic system according to a certain embodiment, the medical image diagnostic apparatus may perform transmission according to the result of comparing the collected incident data with the threshold. In this case, if the verification result has revealed that there is no past incident data or information for motion that substantially conforms to the received incident data or information for motion, the server may transmit the threshold update instruction for updating the threshold to the medical image diagnostic apparatus. With this configuration, it is possible to update the threshold when the past information is not available, so that similar abnormalities can be detected in the future.

First Modification

A first modification of the foregoing embodiments will be set forth with reference to FIG. 14.

In the first modification, an X-ray diagnostic apparatus 100*a*, an X-ray CT apparatus 100*b*, or an MRI apparatus 100*c*, in place of the medical image diagnostic apparatus 100 described above, is connected to the server 300 via the network Nw. For the X-ray diagnostic apparatus 100*a*, the X-ray CT apparatus 100*b*, and the MRI apparatus 100*c*, the drawing schematically shows only the configurations for the information about a subject image and motions of mechanisms, and the incident data. The drawing omits the other detailed configurations.

In FIG. 14, each of mechanical systems 101*a*, 101*b*, and 101*c* includes an imaging unit to image a subject, and is used in the X-ray diagnostic apparatus 100*a*, the X-ray CT apparatus 100b, or the MRI apparatus 100c. The mechanical systems 101a, 101b, and 101c each generate an operating sound and shaking during or prior to imaging a subject 150.

For example, the mechanical system 101a is for use by the X-ray diagnostic apparatus 100a, and includes an imager 101a1 with an X-ray generator and an X-ray detector, and an arm to movably support the imager 101a1. The arm represents one example of a mechanism 101a2 that includes a movable part.

The mechanical system 101b is for use by the X-ray CT apparatus 100b, and includes an imager 101b1 with an X-ray generator and an X-ray detector, and a rotary frame to rotatably support the imager 101b1. The rotary frame represents one example of a mechanism 101b2 that includes a movable part.

The mechanical system 101c is for use by the MRI apparatus 100c, and includes an electrically-driven couch on which the subject 150 can be placed. The electrically-driven couch represents one example of a mechanism 101c2 that includes a movable part.

Each of image generators 102a, 102b, and 102c is circuitry for generating a subject image based on the output of the imager 101a1, 101b1, or 101c1.

Each of operating sound processors 103a, 103b, and 103c performs at least one of collecting, storing, transmitting, or analyzing the incident data of the mechanism 101a2, 101b2, or 101c2, based on at least either of the analysis result of the subject image or the information for motion of the mechanism 101a2, 101b2, or 101c2. Note that, when performing transmission, the operating sound processors 103a, 103b, and 103c each transmit the incident data and the information for motion to the server 300.

The server 300 is of similar configurations to those described for the foregoing embodiments.

According to such a first modification, even if a mechanical system is used in any of the X-ray diagnostic apparatus, X-ray CT apparatus, and the MRI apparatus, and generates an operating sound and shaking during or prior to imaging a subject, the same effects as described for the foregoing embodiments can be obtained.

Figure 15:
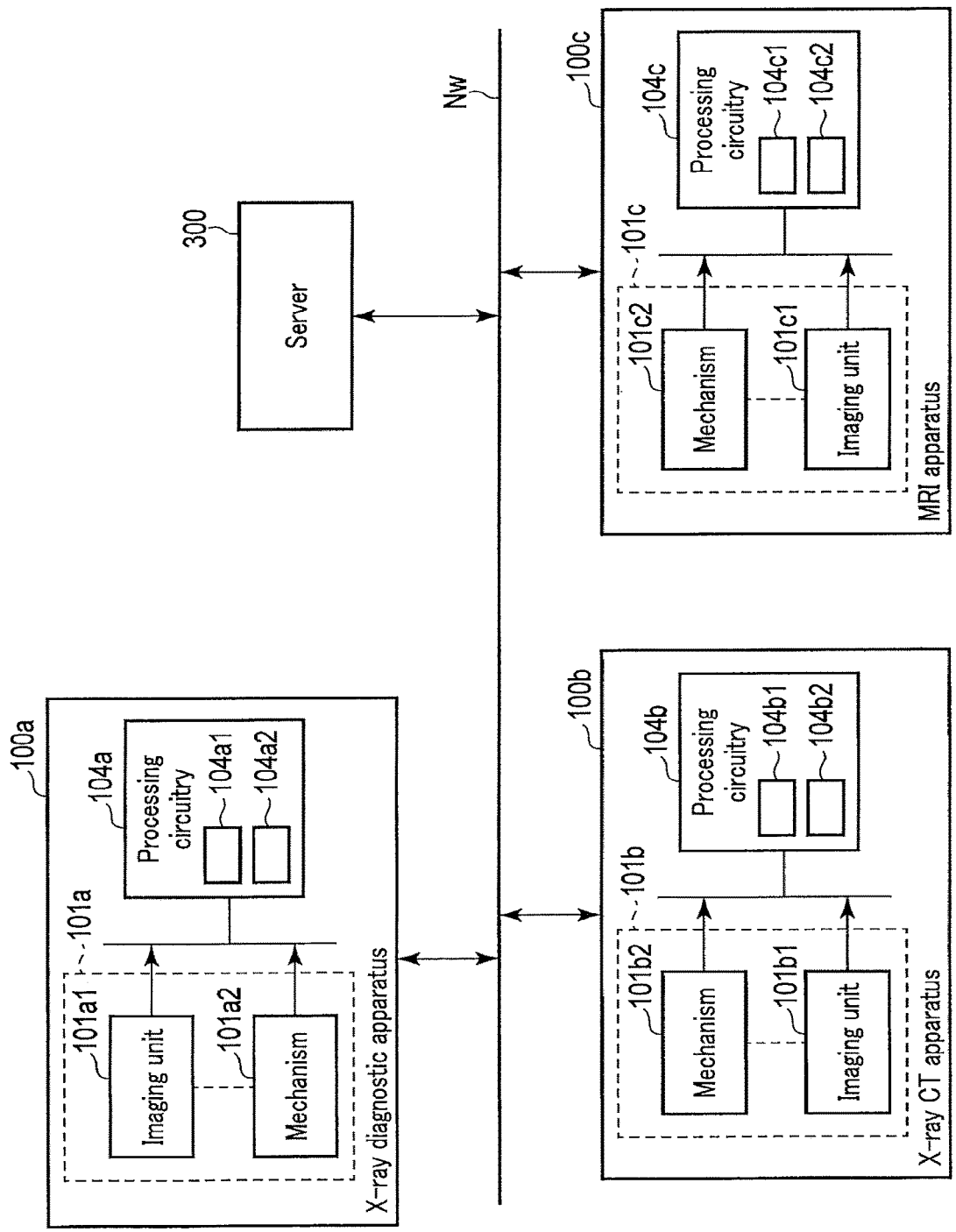
FIG. 15 is a schematic diagram showing a modified configuration of the first modification of the embodiment.

The first modification may be further modified as shown in FIG. 15 to replace the image generators 102a, 102b, and 102c and to replace the operating sound processors 103a, 103b, and 103c. That is, the first modification may be modified so that processing circuitry 104a, 104b, or 104c is adapted to perform corresponding functions 104a1 and 104a2, 104b1 and 104b2, or 104c1 and 104c2.

Here, the processing circuitry 104a, 104b, or 104c is a processor that reads and executes programs in a storage (not shown) to realize an image generation function 104a1, 104b1, or 104c1, and an operating sound processing function 104a2, 104b2, or 104c2, corresponding to the programs.

The image generation functions 104a1, 104b1, and 104c1 are functions corresponding to the image generators 102a, 102b, and 102c described above.

The operating sound processing functions 104a2, 104b2, and 104c2 are functions corresponding to the operating sound processors 103a, 103b, and 103c.

The other configurations are the same as those described for the first modification.

Such a further modification can also provide the same effects as described for the first modification.

Second Modification

Next, a second modification of the foregoing embodiments will be set forth with reference to FIG. 16.

In the second modification, the processing circuitry 23 performs an image generation function 23c, a position information detection function 23d, and a system control function 23e, in place of the image generation circuitry 6, the position information detector 21, and the system control circuitry 26 described above.

That is, the processing circuitry 23 is a processor that reads and executes programs in the storage 22 to realize the operating sound processing function 23a, the receive function 23b, the image generation function 23c, the position information detection function 23d, and the system control function 23e, corresponding to the programs.

Here, the image generation function 23c is a function corresponding to the image generation circuitry 6 described above.

The position information detection function 23d is a function corresponding to the position information detector 21.

The system control function 23e is a function corresponding to the system control circuitry 26.

The other configurations are the same as those described for the foregoing embodiments.

According to this second modification that adopts a configuration of the processing circuitry 23 to perform the image generation function 23c, the position information detection function 23d, and the system control function 23e, the same effects as described for the foregoing embodiments can be obtained.

Third Modification

Figure 17:
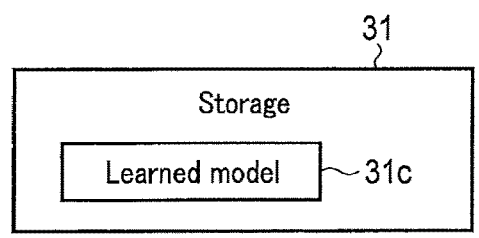
FIG. 17 is a schematic diagram for explaining a server's storage and a learned model according to a third modification of the embodiment.
Figure 18:
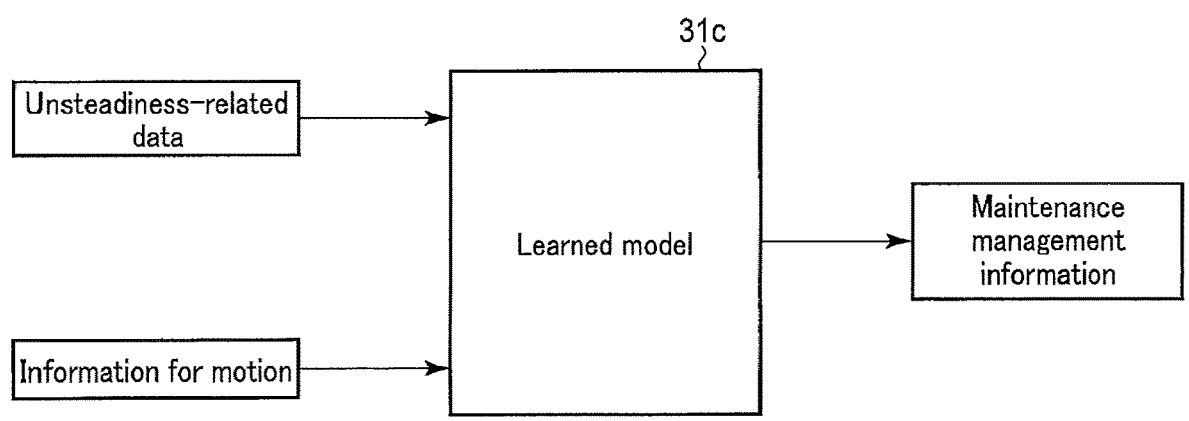
FIG. 18 is a schematic diagram for explaining the learned model according to the third modification of the embodiment.

Next, a third modification of the foregoing embodiments will be set forth with reference to FIGS. 17 and 18.

In the third modification, the server 300 acquires the maintenance management information using AI. More specifically, according to the third modification, the storage 31 of the server 300 stores a learned model 31c as shown in FIGS. 17 and 18, and a model learning program (not shown), in place of the history table 31a, the operating sound management table 31b, the various thresholds, and the acceptable value in the foregoing description. The learned model 31c has undergone learning processes using the past incident data and information for motion, as well as the maintenance management information associated with the past information for motion.

The learned model 31c here is a learned machine learning model that has been obtained by subjecting a machine learning model to machine learning processes using learning data based on the model learning program. The learning data contains input data and output data. The input data includes the incident data and the information for motion. The output data includes the maintenance management information. The learning data may also contain a model number or an apparatus ID of the medical image diagnostic apparatus 100 as the input data, in addition to the incident data and the information for motion. The machine learning model is a parameterized composite function in which multiple functions are synthesized, and it is adapted to output the maintenance management information using the incident data and the information for motion as inputs. The parameterized composite function is defined by the combination of multiple adjustable functions and parameters. The machine learning model according to this modification may adopt any parameterized composite functions as long as the above role is served, but it will be assumed that the machine learning model here is a multi-layered network model (hereinafter, "multi-layered network"). The learned model 31c in this case includes an input layer for inputting the incident data and the information for motion, an output layer for outputting the maintenance management information associated with the incident data and the information for motion, and at least one intermediate layer provided between the input layer and the output layer. As the multi-layered network, for example, a deep neural network (DNN) which is a multi-layered neural network intended for deep learning is adopted. As the DNN, for example, a recurrent neural network (RNN) which is intended for group data such as sounds, languages, and moving images may be used. This learned model 31*c* is expected to be utilized as a program module constituting part of artificial intelligence software. The learned model 31*c* is for use by the processing circuitry 32.

The processing circuitry 32 uses the learned model 31*c* to acquire the maintenance management information from the incident data and the information for motion. More specifically, the processing circuitry 32 follows the instructions of the learned model 31*c* stored in the storage 31 to perform, based on learned parameters, arithmetic operations on the incident data and the information for motion which have been input to the input layer, so that the maintenance management information will be output from the output layer.

The other configurations are the same as those described for the foregoing embodiments.

According to this third modification, the learned model is used to acquire the maintenance management information from the incident data and the information for motion. Therefore, the same effects as described for the foregoing embodiments can be obtained even without a configuration to store the incident data, the information for motion, and the maintenance management information in association with each other.

Also, the learned model has undergone learning processes using the past incident data and information for motion as well as the maintenance management information associated with the past information for motion. Therefore, the same effects as described for the foregoing embodiments can be obtained while omitting the server administrator's labor of editing the maintenance management information.

Note that this third modification is not necessarily required to omit the history table 31*a*, the operating sound management table 31*b*, the various thresholds, the acceptable value, or the like, given in the foregoing disclosure. When such features are present, the processing circuitry 32 may apply the use of the learned model 31*c* to acquisition and update of the maintenance management information, and may transmit the threshold update instruction to the medical image diagnostic apparatus 100 so that the thresholds will be updated based on the updated maintenance management information. In this manner, too, the same effects as described for the foregoing embodiments can be obtained while omitting the server administrator's labor of editing the maintenance management information.

Fourth Modification

Next, a fourth modification of the foregoing embodiments, relating to the second modification, will be set forth with reference to FIGS. 16 and 19.

In the fourth modification, the operating sound data or the shaking data of the mechanisms is not a requisite, but may be omitted. To facilitate the understanding, the following description will assume an example where both the operating sound data and the shaking data are omitted. As such, the processing circuitry 23 of the medical image diagnostic apparatus 100, as shown in FIG. 16, utilizes the image generation function 23*c* to generate a subject image based on the output of the X-ray imager 1, and utilizes the operating sound processing function 23*a* to perform processing for the information for motion of the mechanism based on the analysis result of the subject image. The processing here includes at least one of collecting, storing, or transmitting the information for motion. If the operating sound data or the shaking data is not omitted, the processing circuitry 23 may perform at least one of collecting, storing, or transmitting the incident data, in addition to the processing for the information for motion. Also, the information for motion may contain information for a motion amount of the mechanism's movable part. As described above, the position information and the rotation number are each adoptable as the information for a motion amount. Since the operating sound data is not used, the name "operating sound processing function" may be changed to "information processing function", etc., as appropriate.

The other configurations are the same as those described for the second modification.

Figure 19:
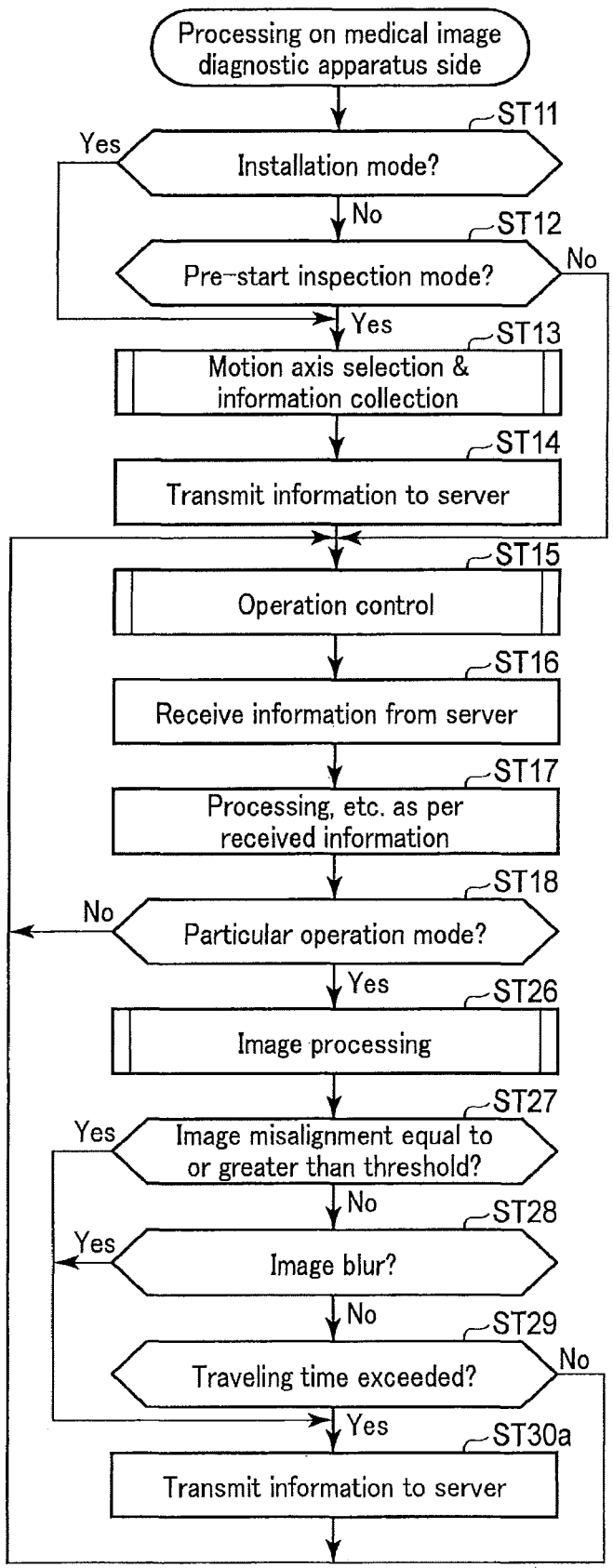
FIG. 19 is a flowchart for explaining operations according to a fourth modification of the embodiment.

As shown in FIG. 19, the fourth modification as such does not carry out steps ST19 to ST25 that relate to the operating sound data and the shaking data as described above. The processing flow of the fourth modification proceeds with steps ST11 to ST17 and ST26 to ST29 in the same manner as described above, and then advances to step ST30*a*. In step ST30*a*, the processing circuitry 23 performs processing for the information for motion of the mechanism based on the analysis result of the subject image. That is, if the analysis result of the subject image indicates an abnormality, processing is performed for the information for motion of the mechanism. The instances of abnormality indication include, as described above, when the pixel shift value is equal to or greater than the acceptable value, when the position gap between images is equal to or greater than the acceptable value, when an artifact is detected, and so on. Also, the processing that can be performed in step ST30*a* includes at least one of collecting, storing, or transmitting the information for motion. In one example of step ST30*a*, all of collecting, storing, and transmitting the information for motion are performed. That is, in step ST30*a*, the medical image diagnostic apparatus 100 may collect and store the information for motion, and transmit the information for motion to the server 300.

On the other hand, if the analysis result of the subject image does not indicate an abnormality, the processing for the information for motion is not performed. Also, irrespective of whether or not the analysis result of the image indicates an abnormality, none of collecting, storing, or transmitting the operating sound data or the shaking data is performed. Therefore, the fourth modification can reduce the amount of data processed for the operating sound data and the shaking data, as well as the information for motion, and realize efficient maintenance management.

Also, the information for motion may be information for a motion amount of the movable part. Therefore, if the analysis result of the subject image indicates an abnormality, it is possible to perform processing for the information for a motion amount of the movable part.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image diagnostic apparatus comprising:
an imager configured to image a subject;
a movable mechanism; and
processing circuitry configured to
generate an image of the subject based on an output of the imager,
constantly collect operating sound data of the moveable mechanism, and
perform processing for the collected operating sound data responsive to an abnormality in the collected operating sound data as a trigger, wherein the processing for the collected operating sound data comprises transmitting the collected operating sound data when the collected operating sound data includes an abnormality and not transmitting the collected operating sound data when the collected operating sound data includes no abnormality,
wherein the medical image diagnostic apparatus is an X-ray diagnostic apparatus, an X-ray computed tomography (CT) apparatus, or a magnetic resonance imaging (MRI) apparatus, and
if the medical image diagnostic apparatus is the X-ray diagnostic apparatus, the moveable mechanism is an arm configured to movably support the imager comprising an X-ray generator and an X-ray detector,
if the medical image diagnostic apparatus is the X-ray CT apparatus, the moveable mechanism is a rotary frame configured to rotatably support the imager comprising an X-ray generator and an X-ray detector, and
if the medical image diagnostic apparatus is the MRI apparatus, the moveable mechanism is an electrically-driven couch on which the subject is placed.

2. The medical image diagnostic apparatus according to claim 1, wherein the processing for the collected operating sound data further comprises at least one of storing and analyzing the collected operating sound data.

3. The medical image diagnostic apparatus according to claim 2, wherein, in the transmitting, the processing circuitry is configured to transmit the collected operating sound data and information for motion of the moveable mechanism.

4. The medical image diagnostic apparatus according to claim 3, wherein the information for motion comprises an electric-current value for a motor for driving the movable mechanism.

5. The medical image diagnostic apparatus according to claim 4, wherein the processing circuitry is configured to collect the operating sound data and the information for motion, and to perform the processing for the operating sound data responsive to a condition for the electric-current value being satisfied.

6. The medical image diagnostic apparatus according to claim 1, wherein the processing circuitry is configured to specify an inter-image position gap, and to perform the processing for the collected operating sound data responsive to a condition for the position gap being satisfied.

7. The medical image diagnostic apparatus according to claim 1, wherein the processing circuitry is configured to perform image reconstruction based on a plurality of imaging by the imager, and to perform the processing for the collected operating sound data responsive to a condition for an artifact in an image obtained by the image reconstruction being satisfied.

8. The medical image diagnostic apparatus according to claim 3, wherein the information for motion comprises a traveling time for the imager to move by a predetermined interval, and
the processing circuitry is configured to collect and store the operating sound data and the information for motion, and to transmit the stored operating sound data and the stored information for motion responsive to a condition for the traveling time being satisfied.

9. A medical image diagnostic system comprising:
a medical image diagnostic apparatus; and
a server system comprising at least one server,
wherein
the medical image diagnostic apparatus comprises:
an imager configured to image a subject;
a movable mechanism; and
first processing circuitry configured to
generate an image of the subject based on an output of the imager,
constantly collect operating sound data of the moveable mechanism, and
transmit the collected operating sound data and information for motion of the moveable mechanism to the at least one server responsive to an abnormality in the collected operating sound data as a trigger but not to transmit the collected operating sound data when the collected operating sound data includes no abnormality, and
the server system comprises
a second processing circuitry configured to
acquire, responsive to receiving the collected operating sound data and the information for motion from the medical image diagnostic apparatus, maintenance management information associated with the received operating sound data and the received information for motion, and
transmit the acquired maintenance management information to the medical image diagnostic apparatus,
wherein the medical image diagnostic apparatus is an X-ray diagnostic apparatus, an X-ray computed tomography (CT) apparatus, or a magnetic resonance imaging (MRI) apparatus, and
if the medical image diagnostic apparatus is the X-ray diagnostic apparatus, the moveable mechanism is an arm configured to movably support the imager comprising an X-ray generator and an X-ray detector,
if the medical image diagnostic apparatus is the X-ray CT apparatus, the moveable mechanism is a rotary frame configured to rotatably support the imager comprising an X-ray generator and an X-ray detector, and
if the medical image diagnostic apparatus is the MRI apparatus, the moveable mechanism is an electrically-driven couch on which the subject is placed.

10. The medical image diagnostic system according to claim 9, wherein the server system further comprises a storage configured to store past operating sound data and past information for motion in association with maintenance management information for the movable mechanism, and
the second processing circuitry is configured to acquire the maintenance management information associated with the received operating sound data and the received information for motion, from the storage.

11. The medical image diagnostic system according to claim 10, wherein the second processing circuitry is configured to
- verify the received operating sound data and the received information for motion, against the past operating sound data and the past information for motion in the storage, and
- if the past operating sound data and the past information for motion are verified as substantially conforming to the received operating sound data and the received information for motion, acquire maintenance management information associated with the past operating sound data and the past information for motion from the storage.

12. The medical image diagnostic system according to claim 11, wherein
- the first processing circuitry is configured to collect the operating sound data and perform the transmitting based on a comparison between the collected operating sound data and a threshold, and
- the second processing circuitry is configured to transmit, if the past operating sound data and the past information for motion are verified as not substantially conforming to the received operating sound data and the received information for motion, a threshold update instruction for updating the threshold to the medical image diagnostic apparatus.

13. The medical image diagnostic system according to claim 9, wherein the server system further comprises a storage configured to store a learned model, and
- the second processing circuitry is configured to use the learned model to acquire the maintenance management information from the operating sound data and the information for motion.

14. The medical image diagnostic system according to claim 13, wherein
- the first processing circuitry is configured to collect the operating sound data and perform the transmitting based on a comparison between the collected operating sound data and a threshold, and
- the second processing circuitry is configured to use the learned model to acquire and update the maintenance management information, and to transmit a threshold update instruction to the medical image diagnostic apparatus so that the threshold is updated based on the updated maintenance management information.

15. The medical image diagnostic system according to claim 13, wherein the learned model undergoes a learning process using past operating sound data, past information for motion, and maintenance management information associated with the past information for motion.

16. A medical image diagnostic apparatus comprising:
an imager configured to image a subject;
a movable mechanism comprising; and
processing circuitry configured to
- generate an image of the subject based on an output of the imager,
- constantly collect information for motion of the moveable mechanism, and
- perform processing for the collected information for motion responsive to an abnormality in a result of analyzing the image of the subject, wherein the processing for the collected information for motion comprises transmitting the collected information for motion when the result of analyzing includes an abnormality and not transmitting the collected information for motion when the result of analyzing includes no abnormality,
wherein the medical image diagnostic apparatus is an X-ray diagnostic apparatus, an X-ray computed tomography (CT) apparatus, or a magnetic resonance imaging (MRI) apparatus, and
if the medical image diagnostic apparatus is the X-ray diagnostic apparatus, the moveable mechanism is an arm configured to movably support the imager comprising an X-ray generator and an X-ray detector,
if the medical image diagnostic apparatus is the X-ray CT apparatus, the moveable mechanism is a rotary frame configured to rotatably support the imager comprising an X-ray generator and an X-ray detector, and
if the medical image diagnostic apparatus is the MRI apparatus, the moveable mechanism is an electrically-driven couch on which the subject is placed.

17. The medical image diagnostic apparatus according to claim 16, wherein the processing for the collected information for motion further comprises storing the collected information for motion.

18. The medical image diagnostic apparatus according to claim 16, wherein the collected information for motion comprises information for a motion amount of the movable mechanism.

19. The medical image diagnostic apparatus as claimed in claim 1, wherein the processing circuitry configured to constantly collect the operating sound data comprises processing circuitry configured to constantly collect shaking data of the moveable mechanism from an acceleration sensor.

20. The medical image diagnostic apparatus as claimed in claim 9, wherein the first processing circuitry configured to constantly collect the operating sound data comprises processing circuitry configured to constantly collect shaking data of the moveable mechanism from an acceleration sensor.

* * * * *